US010792494B2

(12) United States Patent
Matsushita

(10) Patent No.: US 10,792,494 B2
(45) Date of Patent: Oct. 6, 2020

(54) EXERCISE INSTRUMENT CONTROLLER AND EXERCISE INSTRUMENT CONTROL PROGRAM

(71) Applicant: MTG CO., LTD., Nagoya, Aichi (JP)

(72) Inventor: Tsuyoshi Matsushita, Nagoya (JP)

(73) Assignee: MTG CO., LTD., Nagoya, Aichi (JP)

( * ) Notice: Subject to any disclaimer, the term of this patent is extended or adjusted under 35 U.S.C. 154(b) by 404 days.

(21) Appl. No.: 15/713,241

(22) Filed: Sep. 22, 2017

(65) Prior Publication Data

US 2018/0304074 A1 Oct. 25, 2018

(30) Foreign Application Priority Data

Apr. 24, 2017 (JP) ................................. 2017/085669

(51) Int. Cl.
*A61N 1/36* (2006.01)
*A61N 1/04* (2006.01)
*A61N 1/32* (2006.01)

(52) U.S. Cl.
CPC ....... *A61N 1/36003* (2013.01); *A61N 1/0452* (2013.01); *A61N 1/0492* (2013.01); *A61N 1/3603* (2017.08); *A61N 1/0484* (2013.01); *A61N 1/321* (2013.01)

(58) Field of Classification Search
CPC ........................... A61N 1/36003; A61N 1/0452
USPC .......................................................... 607/48
See application file for complete search history.

(56) References Cited

U.S. PATENT DOCUMENTS

2015/0202429 A1 7/2015 Fritzsche
2016/0303363 A1* 10/2016 Girouard ........................ 1/452

FOREIGN PATENT DOCUMENTS

| JP | 2004216031 A | 8/2004 |
| JP | 2017006644 A | 1/2017 |
| JP | 2017-006644 | 12/2017 |
| WO | WO2007081607 A2 | 7/2007 |
| WO | WO2016131926 A1 | 8/2016 |
| WO | WO 2016/149564 A1 | 9/2016 |

* cited by examiner

*Primary Examiner* — Nadia A Mahmood
(74) *Attorney, Agent, or Firm* — Muncy, Geissler, Olds & Lowe, P.C.

(57) ABSTRACT

In an exercise instrument controller, a type determination unit specifies, from among a plurality of types, the type of exercise for which an exercise instrument is used. An association determination unit specifies association between a body part that is exercised and the exercise instrument based on the type that has been specified. A setting processing unit sets an operation detail of the exercise instrument based on user's manipulation. An instrument control unit controls, by transmitting information indicating an operation detail for each exercise instrument based on the association between the body part and the exercise instrument that has been specified and the operation detail that has been set, exercise by the exercise instrument. A display control unit controls a screen display regarding the association between the body part and the exercise instrument, the operation detail, and an exercising status.

6 Claims, 18 Drawing Sheets

FIG.8

| | Abs | Abs +Waist | Arm | Leg | Body | NUMBER OF CONNECTED DEVICES | ICONS TO BE DISPLAYED = DEVICES TO BE DISCONNECTED | ERROR TEXT |
|---|---|---|---|---|---|---|---|---|
| 1 DEVICE | 2 | | | | | 2 | 2 Abs | *TWO OR MORE Abs INSTRUMENTS CANNOT BE USED AT THE SAME TIME. |
| | | 2 | | | | 2 | 2 Abs+Waist | *TWO OR MORE Abs + Waist INSTRUMENTS CANNOT BE USED AT THE SAME TIME. |
| | | | 2 | | | 2 | 2 Arm | PLEASE DO NOT TRAIN BOTH ARMS AT THE SAME TIME FOR SAFETY PURPOSES. *TWO OR MORE Arm INSTRUMENTS CANNOT BE USED AT THE SAME TIME. |
| | | | | 3 | | 3 | 3 Leg | *THREE OR MORE Leg INSTRUMENTS CANNOT BE USED AT THE SAME TIME. |
| | | | | | 6 | 6 | 6 Body | *SIX OR MORE Body INSTRUMENTS CANNOT BE USED AT THE SAME TIME. |
| 2 DEVICES | 1 | 1 | | | | 2 | 2 Abs | *Abs INSTRUMENT AND Abs + Waist INSTRUMENT CANNOT BE USED AT THE SAME TIME. |
| | | | 1 | | 4 | 5 | 5 Body | *EXCEEDING THE NUMBER OF PARTS THAT CAN BE TRAINED BY THE NUMBER OF DEVICES THAT ARE WORN. |
| | | | | 1 | 5 | 6 | 6 Body | *EXCEEDING THE NUMBER OF PARTS THAT CAN BE TRAINED BY THE NUMBER OF DEVICES THAT ARE WORN. |
| | | | 1 | | 5 | 6 | 6 Body | *EXCEEDING THE NUMBER OF PARTS THAT CAN BE TRAINED BY THE NUMBER OF DEVICES THAT ARE WORN. |
| | | | | 2 | 4 | 6 | 6 Body | *EXCEEDING THE NUMBER OF PARTS THAT CAN BE TRAINED BY THE NUMBER OF DEVICES THAT ARE WORN. |
| 3 DEVICES | | | 1 | 1 | 3 | 5 | 5 Body | *EXCEEDING THE NUMBER OF PARTS THAT CAN BE TRAINED BY THE NUMBER OF DEVICES THAT ARE WORN. |
| | | | 1 | 1 | 3 | 5 | 5 Body | *EXCEEDING THE NUMBER OF PARTS THAT CAN BE TRAINED BY THE NUMBER OF DEVICES THAT ARE WORN. |
| | | | 1 | 2 | 2 | 5 | 5 Body | *EXCEEDING THE NUMBER OF PARTS THAT CAN BE TRAINED BY THE NUMBER OF DEVICES THAT ARE WORN. |
| | | | | 1 | 4 | 5 | 5 Body | *EXCEEDING THE NUMBER OF PARTS THAT CAN BE TRAINED BY THE NUMBER OF DEVICES THAT ARE WORN. |
| | | | | 2 | 3 | 5 | 5 Body | *EXCEEDING THE NUMBER OF PARTS THAT CAN BE TRAINED BY THE NUMBER OF DEVICES THAT ARE WORN. |
| 4 DEVICES | | | 1 | 1 | 2 | 4 | 6 Body | *EXCEEDING THE NUMBER OF PARTS THAT CAN BE TRAINED BY THE NUMBER OF DEVICES THAT ARE WORN. |
| | | | 1 | 1 | 1 | 3 | 5 Body | *EXCEEDING THE NUMBER OF PARTS THAT CAN BE TRAINED BY THE NUMBER OF DEVICES THAT ARE WORN. |

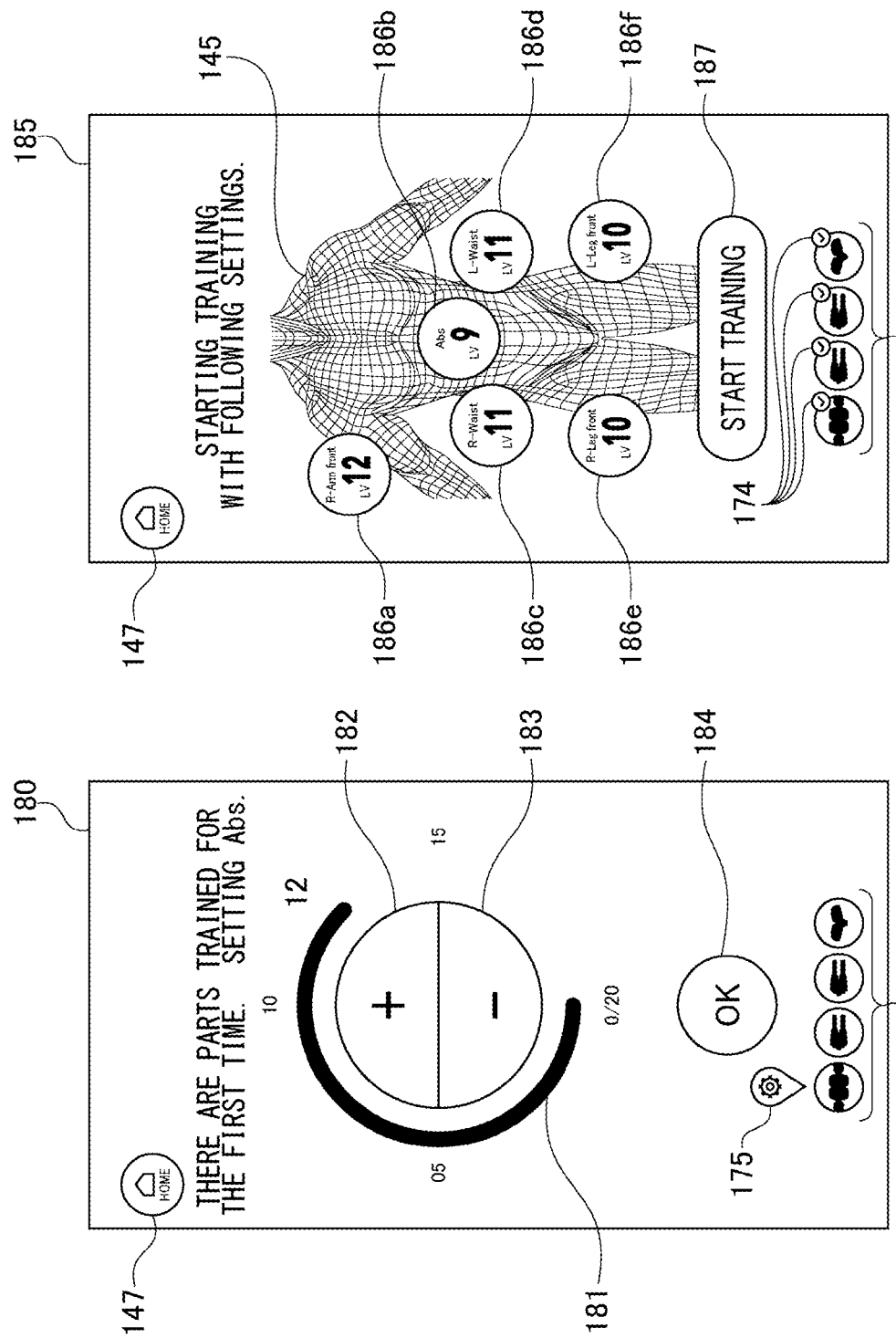

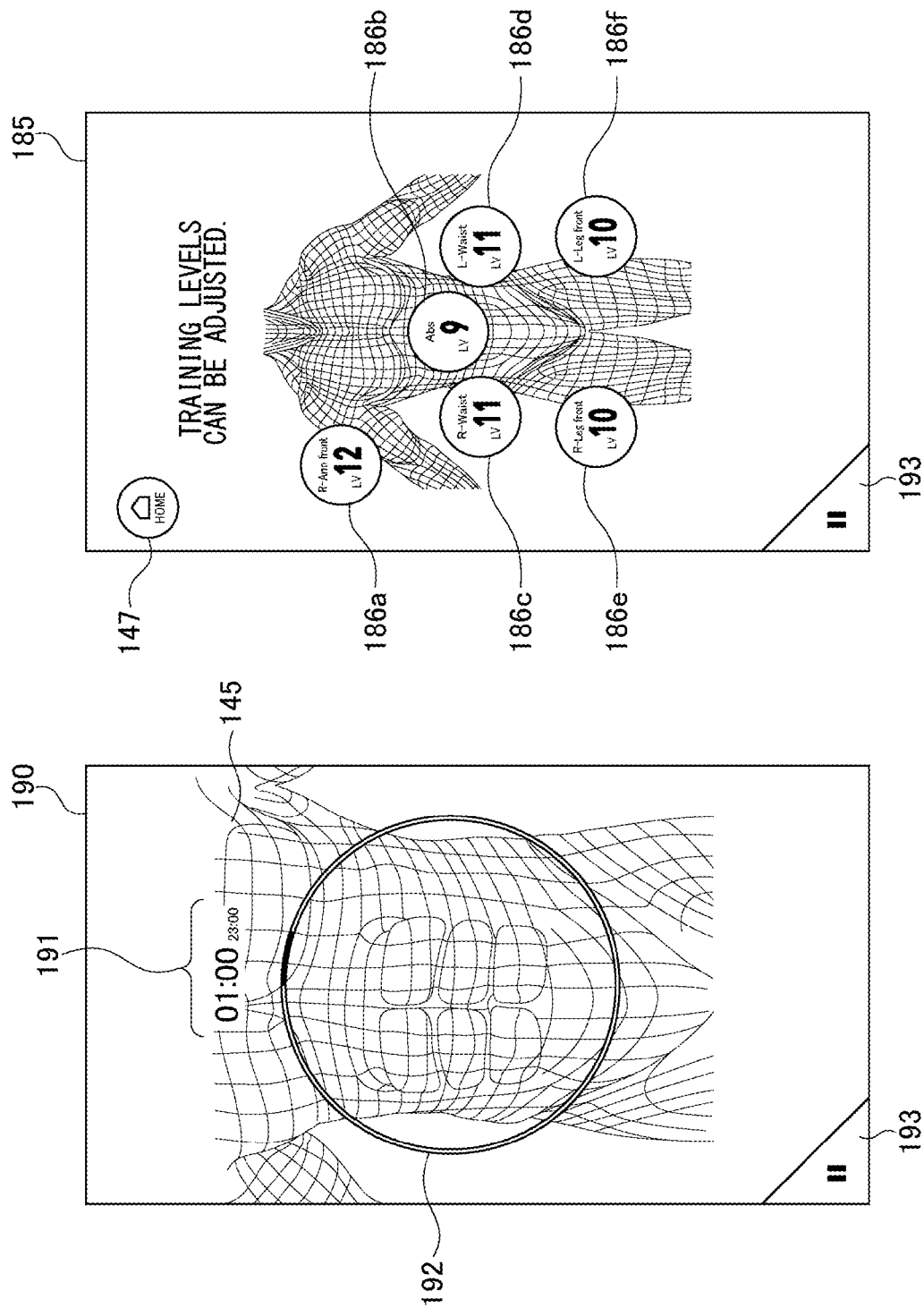

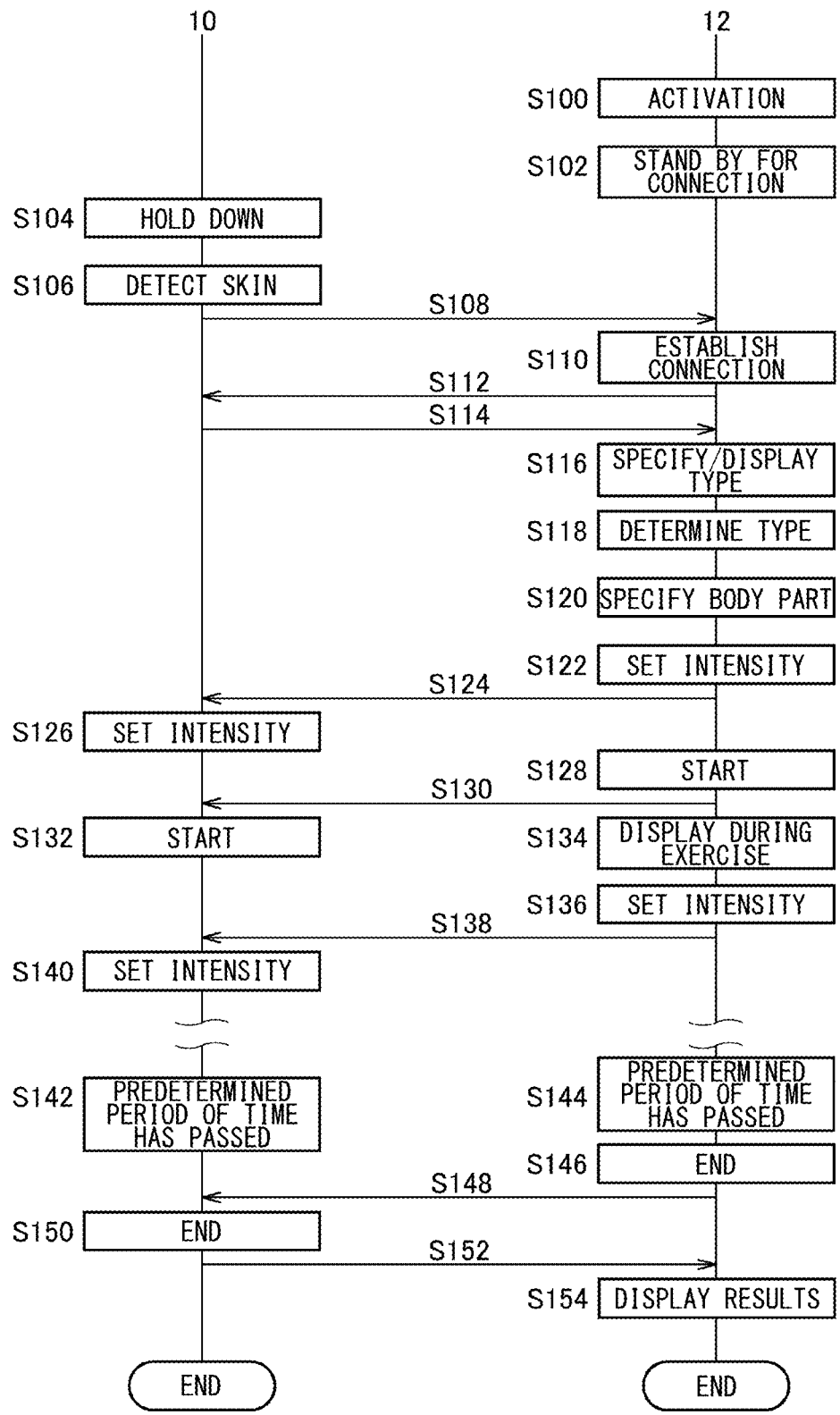

EXERCISE INSTRUMENT CONTROLLER AND EXERCISE INSTRUMENT CONTROL PROGRAM

BACKGROUND OF THE INVENTION

1. Field of the Invention

The present invention relates to an exercise instrument controller.

2. Description of the Related Art

Exercise instruments used for human physical exercise include, for example, electrical muscle stimulation (EMS) devices. Electrical muscle stimulation devices are expected to exercise muscles for muscle strengthening by applying a weak electric current to the muscles so as to stress or relax the muscles. Conventionally, for example, an electrical muscle stimulation device described in patent document 1 is proposed.

[Patent Document 1] JP2017-6644

Among users of electrical muscle stimulation devices, there are more than a few users who wish to build up muscles without any effort or lose weight without any effort. In order to encourage such users to continue using the devices, an improvement in the efficiency and user-friendliness in usage is required.

SUMMARY OF THE INVENTION

In this background, a purpose of the present invention is to provide an exercise instrument controller capable of efficiently controlling an exercise instrument used for multiple body parts.

An exercise instrument controller according to one embodiment of the present invention includes: a communication processing unit that receives information via a predetermined communication means from an exercise instrument used for physical exercise; a type determination unit that specifies, from among a plurality of types, the type of exercise for which the exercise instrument is used based on the information that has been received; an association determination unit that specifies association between a body part that is exercised and the exercise instrument based on the type that has been specified; a setting processing unit that sets an operation detail of the exercise instrument based on manipulation input by the user via a manipulation means; an instrument control unit that controls, by transmitting information indicating the operation detail via the predetermined communication means for each exercise instrument based on the association between the body part and the exercise instrument that has been specified and the operation detail that has been set, exercise by the exercise instrument; and a display control unit that controls screen display related to the association between the body part and the exercise instrument, the operation detail, and an exercising status. Based on a plurality of types of exercise specified for a plurality of exercise instruments, the association determination unit can specify association of the plurality of body parts respectively with different exercise instruments, and the setting processing unit can set different operation details respectively for the plurality of body parts.

Optional combinations of the aforementioned constituting elements, and implementations of the invention in the form of methods, apparatuses, programs, recording mediums recording programs, and systems may also be practiced as additional modes of the present invention.

BRIEF DESCRIPTION OF THE DRAWINGS

Embodiments will now be described, by way of example only, with reference to the accompanying drawings that are meant to be exemplary, not limiting, and wherein like elements are numbered alike in several figures, in which:

FIG. 8 is a diagram schematically showing a prohibition table that sets prohibition standards;

FIGS. 12A-12B are diagrams schematically showing an intensity setting screen;

FIGS. 13A-13B are diagrams schematically showing an exemplary screen displayed during exercise;

FIG. 18 is a time chart schematically showing the transmission and/or reception of information between the muscle electrostimulation device and the exercise instrument controller.

DETAILED DESCRIPTION OF THE INVENTION

Figure 1:
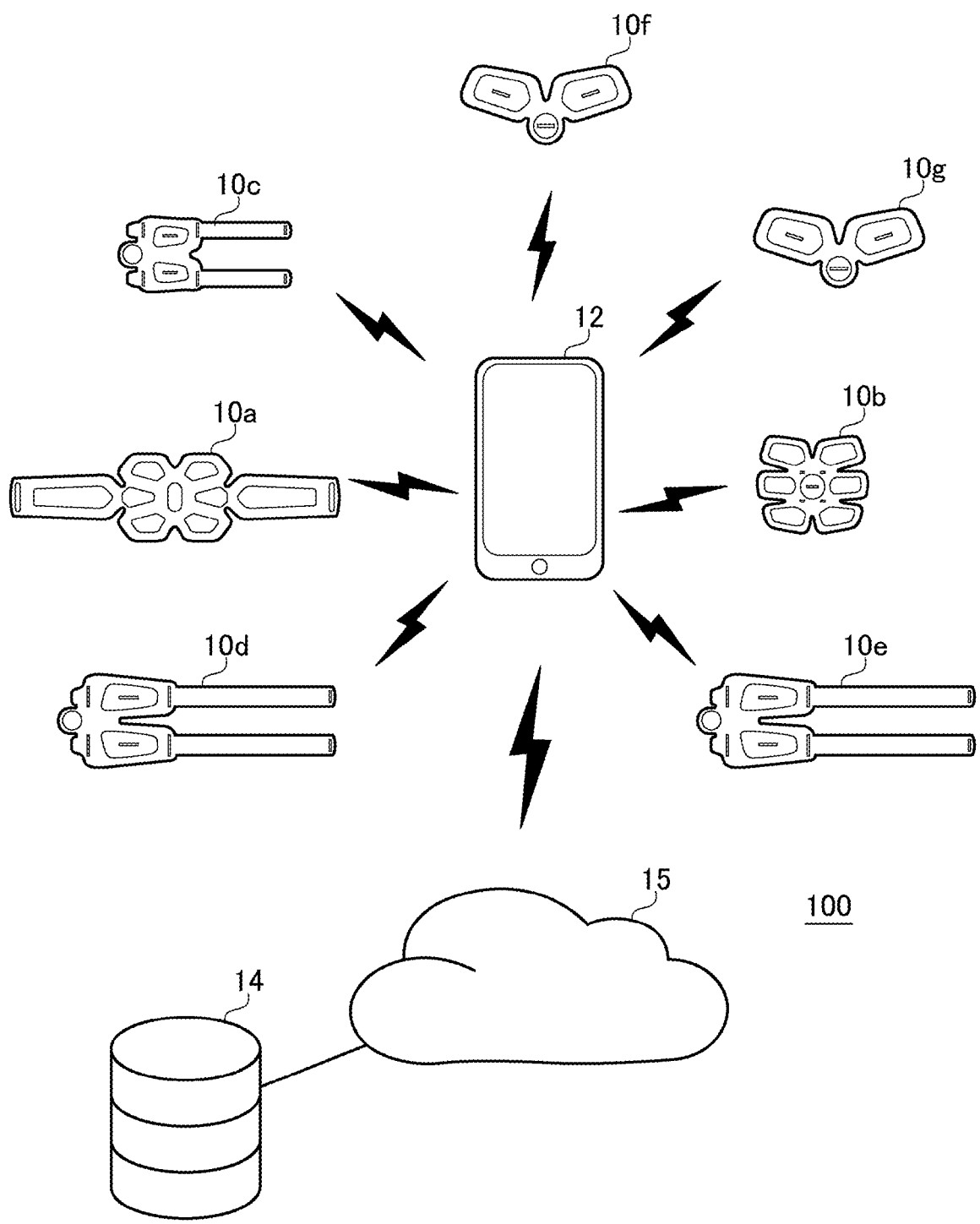
FIG. 1 is a schematic diagram showing an exercise instrument control system according to an embodiment.

The invention will now be described by reference to the preferred embodiments. This does not intend to limit the scope of the present invention, but to exemplify the invention.

Among users of muscle electrostimulation devices, there are more than a few users who wish to build up muscles without any effort or lose weight without any effort. In order to encourage such users to continue using the muscle electrostimulation devices, the users are preferably allowed to see the results of exercise and the effects of the exercise as the outcome of the exercise in addition to easy settings and manipulations of the devices. There are users who wish to use a plurality of devices easily at the same time. There is also a case where users wish to use a certain device on a plurality of body parts while switching the body parts. In the case where a plurality of devices can be used at the same time on a plurality of body parts, there is a high user demand for user-friendliness in order to allow for easier settings and manipulations. Such a challenge also applies to not just a muscle electrostimulation device but also an arbitrary exercise instrument.

An exercise instrument controller according to the present embodiment includes: a communication processing unit that receives information via a predetermined communication means from an exercise instrument used for physical exercise; a type determination unit that specifies, from among a plurality of types, the type of exercise for which the exercise instrument is used based on the information that has been received; an association determination unit that specifies association between a body part that is exercised and the exercise instrument based on the type that has been specified; a setting processing unit that sets an operation detail of the exercise instrument based on manipulation input by the user via a manipulation means; an instrument control unit that controls, by transmitting information indicating the operation detail via the predetermined communication means for each exercise instrument based on the association between the body part and the exercise instrument that has been specified and the operation detail that has been set, exercise by the exercise instrument; and a display control unit that controls screen display related to the association between the body part and the exercise instrument, the operation detail, and an exercising status. Based on a plurality of types of exercise specified for a plurality of exercise instruments, the association determination unit can specify association of the plurality of body parts respectively with different exercise instruments, and the setting processing unit can set different operation details respectively for the plurality of body parts.

In addition to muscle electrostimulation devices that support physical exercise for creatures including humans, the "exercise instruments" used here may include exercise instruments used for the purpose of various sports and beauty care. In addition to wireless communication such as short-distance wireless communication and wireless LAN, the "predetermined communication means" may include various communication means including wire communication means. The "type of exercise" may be the type of an exercise instrument or may be the type of a body part that can be exercised using the exercise instrument. At least, for distinction from one another, it is satisfactory as long as the "type of exercise" is a concept that can be distinguished based on the type of an exercise instrument or a concept that can be distinguished based on the type of a body part that can be exercised using the exercise instrument. The "operation details" may be, in the case of, for example, a muscle electrostimulation device, a setting related to the intensity of electrostimulation by the muscle electrostimulation device or may be other parameters for determining the operation details or control details of an exercise instrument such as exercise time, the number of exercise, a frequency, and the type of a waveform pattern. The "predetermined manipulation means" may be a manipulation means such as a touch panel provided in the exercise instrument controller or may be a manipulation means such as a setting button provided in the exercise instrument. The "exercise instrument controller" may be, besides a mobile phone terminal called smartphone, various sorts of information terminal including a portable terminal such as a tablet terminal, a game device, etc., and a computer.

According to this embodiment, a plurality of exercise instruments that are used on a plurality of body parts can be easily set or manipulated for each body part. Moreover, the setting and control status of an exercise instrument can be effectively visualized. An increase in the user-friendliness can effectively support the continuation of exercise using the exercise instrument.

The communication processing unit may receive information from a plurality of types of exercise instruments, and the information that is received may have different contents for each type of the exercise instruments. The type determination unit may store, for each type of an exercise instrument, the type of exercise that can be done using an exercise instrument of the type in advance and specify the type of exercise by specifying the type of an exercise instrument based on the information that is received. The association determination unit may store, for each type of exercise, one or more body parts that can be exercised according to the type in advance and specify, in a case where there are a plurality of body parts that can be exercised according to the type of exercise, the association between any of the body parts and an exercise instrument based on manipulation input entered via the predetermined manipulation means by the user. According to this embodiment, the type of an exercise instrument can be specified based on the information that is received, and the type of exercise that can be done using the exercise instrument can be specified. Thus, even when a plurality of exercise instruments are used at the same time, the exercise instruments can be controlled in a distinguishable manner. Further, since a body part on which an exercise instrument is used only needs to be set only when it is necessary, settings and manipulations can be easily done even when a plurality of exercise instruments are used at the same time.

An exercise instrument may be a muscle electrostimulation device that gives electrostimulation to muscles, and the setting processing unit may set the intensity of the electrostimulation by the muscle electrostimulation device as an operation detail. The display control unit may display an image of a human body model and display an image dynamically showing the movement of a muscle being exercised on a screen in accordance with the control status of the exercise instrument. According to this embodiment, even when a plurality of muscle electrostimulation devices are used on a plurality of body parts, settings and manipulations can be easily done for each body part, and a body part to which electrostimulation is applied can be brought into focus by a visual effect even during the operation of the muscle electrostimulation devices. Thus, the effect of exercise can be increased.

An information management unit may be further included that determines the amount of exercise based on an operation detail that is set and performed for each body part using a coefficient for each body part and records a cumulative exercise amount as a result of exercise for each body part. According to the embodiment, the user can check the effect of exercise based on an objective value, leading the user to have motivation to continue exercising.

The association determination unit may store, in advance, a prohibition standard defining a combination of exercise instruments whose use on a single body part or on related body parts is considered to be excessive use and determine whether the use on a body part that can be exercised according to a specified type is considered to be the excessive use defined in the prohibition standard. The instrument control unit may avoid the connection to an exercise instrument whose use is considered to be the excessive use.

According to this embodiment, an overlapped setting of an exercise instrument can be easily avoided for a body part for which only one exercise instrument can be used at a time. Further, a combination of exercise instruments or a combination of body parts that should be avoided from being used at the same time for safety reasons can be easily avoided.

The same or equivalent constituting elements, members, and steps illustrated in each drawing shall be denoted by the same reference numerals, and duplicative explanations will be omitted appropriately. The dimension of members in the drawings shall be enlarged or reduced as appropriate to facilitate understanding. Some of the members not important for the purpose of describing the embodiments are not shown in the drawings.

<Exercise Instrument Control System>

FIG. 1 is a schematic diagram showing an exercise instrument control system 100 according to an embodiment. The exercise instrument control system 100 is provided with a plurality of muscle electrostimulation devices 10a to 10f as exercise instruments, an information terminal as an exercise instrument controller 12, and an information management server 14 for managing information. A muscle electrostimulation device 10 is fitted to a user. The muscle electrostimulation device 10 is fitted to each body part of a user, for example, such as an abdominal muscle, a flank, an arm, a leg, or the like. The muscle electrostimulation device 10 gives electrostimulation to the muscle of the user by a weak electric current. The plurality of muscle electrostimulation devices 10a to 10f each communicate with the exercise instrument controller 12 by short-distance wireless communication such as Bluetooth (registered trademark) so as to transmit and/or receive information. An exercise instrument control program that is executed by the exercise instrument controller 12 communicates with the plurality of muscle electrostimulation devices 10a to 10f and controls the setting and operation of each of the plurality of muscle electrostimulation devices 10a to 10f. The exercise instrument controller 12 connects with a network 15 via wireless communication such as wireless LAN or mobile telephone communication and transmits and/or receives information to/from an information management server 14. The information management server 14 manages the updating of the exercise instrument control program executed by the exercise instrument controller 12 and receives setting information and result information for exercise from the exercise instrument controller 12 so as to manage the setting information and the result information.

The exercise instrument controller 12 is any of a variety of information terminals manipulated by the user, for example, a mobile phone terminal such as a smartphone, a tablet terminal, or a personal computer. The exercise instrument controller 12 sets respective association relationships between the plurality of muscle electrostimulation devices 10a to 10f and respective body parts for which the muscle electrostimulation devices 10 are used and controls the intensity setting and operation for each muscle electrostimulation devices 10. The intensity setting and manipulation are also possible for a single muscle electrostimulation device 10 alone. The user may manipulate a muscle electrostimulation device 10 directly or via the exercise instrument controller 12. The exercise instrument controller 12 functions as a hub for the plurality of muscle electrostimulation devices 10a to 10f. Thus, it is more efficient for the user to collectively control the plurality of muscle electrostimulation devices 10a to 10f by manipulating the exercise instrument controller 12 than to individually set the plurality of muscle electrostimulation devices 10a to 10f for manipulation.

<Exercise Instrument>

Figure 2A:
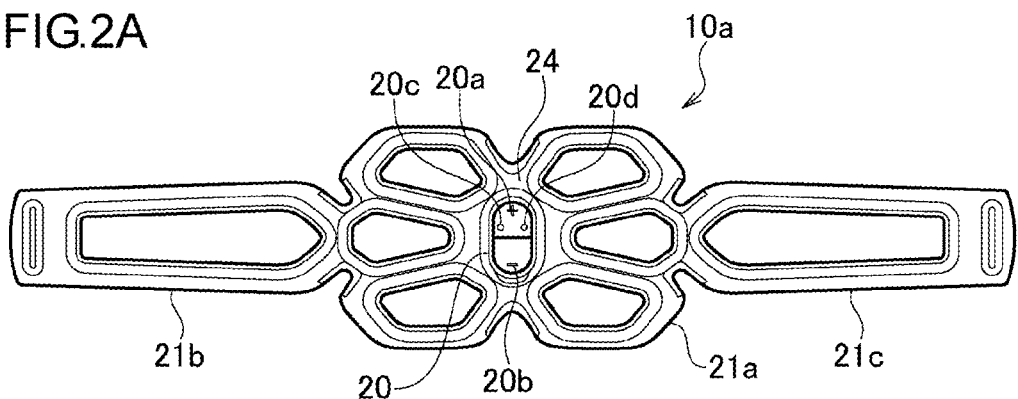
FIGS. 2A-2D are diagrams showing an exemplary exterior view of a muscle electrostimulation device, which is an example of an exercise instrument.
Figure 2B:
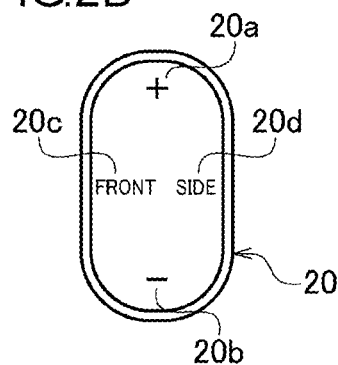
Figure 2C:
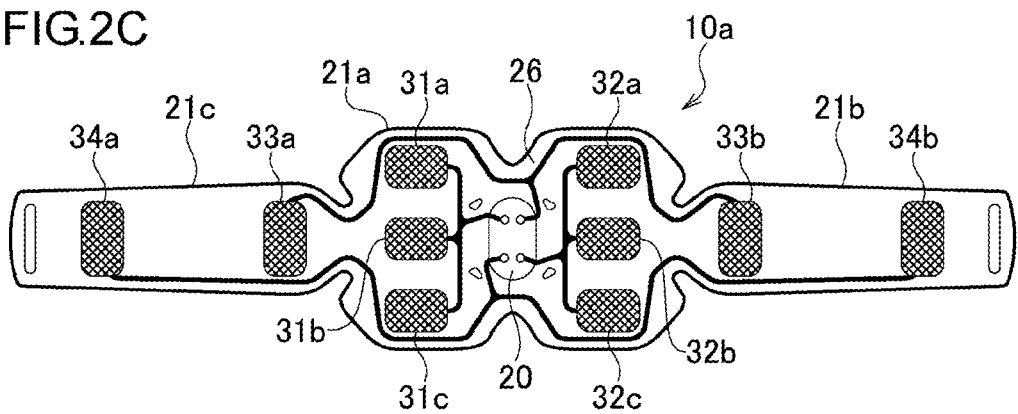
Figure 2D:
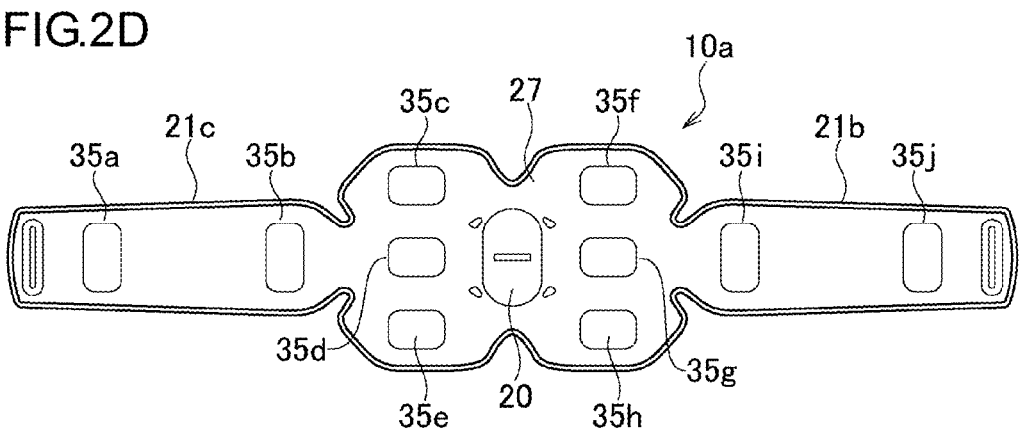

FIGS. 2A-2D show an exemplary exterior view of a muscle electrostimulation device 10, which is an example of an exercise instrument. FIG. 2A is a plan view of the muscle electrostimulation device 10a. FIG. 2B is an enlarged plan view in which a housing portion is enlarged. FIG. 2C is an exterior view of an intermediate member when the muscle electrostimulation device 10a is seen from the back side thereof. FIG. 2D is a back view of the muscle electrostimulation device 10a. The muscle electrostimulation device 10a is provided with a housing 20, a cover 24, a first substrate 26, a second substrate 27, a first electrode group 31, a second electrode group 32, a third electrode group 33, and a fourth electrode group 34. A main body of the muscle electrostimulation device 10a mainly formed of the cover 24, the first substrate 26, and the second substrate 27 includes an abdominal muscle portion 21a, which is a part that is fitted to an abdominal muscle of a person, a right flank portion 21b, which is a part that is fitted to a right flank, and a left flank portion 21c, which is a part that is fitted to a left flank.

The housing 20 is provided in the center of the muscle electrostimulation device 10a. As shown in FIG. 2B, the housing 20 is formed of a resin and has a substantially elliptic shape in a planar view. The housing 20 houses a power supply unit such as a lithium-ion battery and a control unit (both units are described later in FIG. 3). On the top surface side of the housing 20, a plus button 20a, a minus button 20b, an abdominal muscle designation button 20c, and a flank designation button 20d serving as a manipulation unit are provided. The plus button 20a, the minus button 20b, the abdominal muscle designation button 20c, and the flank designation button 20d are formed in a cantilever condition while a portion of the housing 20 is hollowed.

The first substrate 26 and the second substrate 27 are piled up to form a single substrate. The cover 24 is formed of, for example, an elastomer such as silicon. The cover 24 covers the top surface (front surface) side of the first substrate 26 and the housing. In other words, the cover 24, the first substrate 26, and the second substrate 27 are piled up in said order from the top surface side. The cover 24, the first substrate 26, the second substrate 27, and the housing 20 are connected by an adhesive tape or an adhesive agent. A symbol "+" is protrusively formed on a part of the cover 24 that covers the plus button 20a, and a symbol "−" is protrusively formed on a part of the cover 24 that covers the minus button 20b. A letter string "FRONT" is protrusively formed on a part of the cover 24 that covers the abdominal muscle designation button 20c, and a letter string "SIDE" is protrusively formed on a part of the cover 24 that covers the flank designation button 20d. The first substrate 26 and the second substrate 27 are thin sheet-like members and formed of, for example, a resin such as polyethylene terephthalate.

The muscle electrostimulation device 10 includes a set of or a plurality of sets of a pair of positive and negative electrodes. In the case of the muscle electrostimulation device 10a, electrodes 31a to 31c are included in the first electrode group 31, electrodes 32a to 32c are included in the second electrode group 32, electrodes 33a and 33b are included in the third electrode group 33, and electrodes 34a and 34b are included in the fourth electrode group 34. The electrodes are each placed on a back surface of the first substrate 26, that is, a surface that comes into contact with an abdominal muscle or a flank and are exposed through respective openings provided at respective electrode positions in the second substrate 27. The electrodes are each formed of a conductive ink and printed on the back surface of the first substrate 26. There is an electrical current between the electrode 31a and the electrode 32a, between the electrode 31b and the electrode 32b, between the electrode 31c and the electrode 32c, between the electrode 33a and the electrode 34a, and between the electrode 33b and the electrode 34b. In the second substrate 27, openings 35a, 35b, 35c, 35d, 35e, 35f, 35g, 35h, 35i, and 35j are provided at respective positions corresponding to the electrodes 34a, 33a, 31a, 31b, 31c, 32a, 32b, 32c, 33b, and 34b, respectively.

A gel-like adhesive pad (not shown) is attached to the periphery of each opening and to each electrode, and the muscle electrostimulation device 10 is fitted to each body part by the adhesiveness of the adhesive pad. The end portion of the right flank portion 21b and the end portion of the left flank portion 21c are each provided with a long hook and loop fastener band (not shown). The muscle electrostimulation device 10 is fixed by fastening the hook and loop fastener band at an appropriate length after putting the hook and loop fastener band around a person's waist once. The adhesive pad has conductivity, and an electrical current is applied to a body part of the user from each electrode via the adhesive pad. The adhesive pad is changed, for example, when there is a decrease in the adhesiveness or an increase in the electrical resistance due to a decrease in the moisture content, when there is damage, or when dirt shows up, being associated with the use thereof.

In FIGS. 2A-2D, the muscle electrostimulation device 10a, which is a type of a muscle electrostimulation device that is worn on an abdominal muscle and a flank, is illustrated by example. Also for a muscle electrostimulation device 10, which is a type of a muscle electrostimulation device that is worn on another body part, a substrate is formed in a shape that is suitable for wearing the muscle electrostimulation device 10 on the body part, and electrodes in an amount that is suitable for applying an electrical current to the body part are provided. In the following embodiments, the above-described instrument for an abdominal muscle and a flank is also expressed appropriately by an exercise instrument name such as "Abs+Waist", and explanations will be given appropriately using expressions: an instrument for an abdominal muscle "Abs"; an instrument for an arm "Arm"; an instrument for a leg "Leg"; and an instrument for an arbitrary body par "Body".

Figure 3:
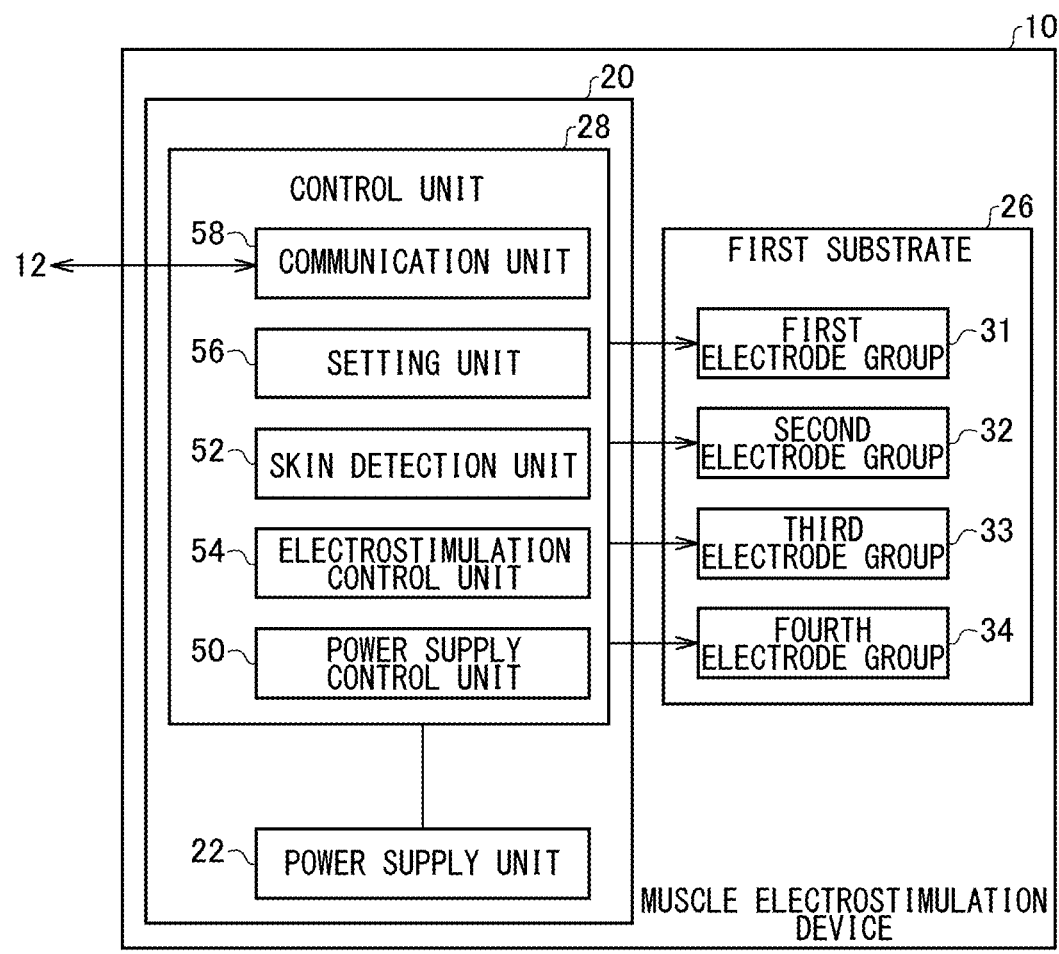
FIG. 3 is a block diagram showing functional features of the muscle electrostimulation device.

FIG. 3 is a block diagram showing functional features of the muscle electrostimulation device 10. The muscle electrostimulation device 10 is provided with a power supply unit 22, a first substrate 26, and a control unit 28. The control unit 28 includes a power supply control unit 50, a skin detection unit 52, an electrostimulation control unit 54, a setting unit 56, and a communication unit 58. The power supply unit 22 is a secondary battery such as a lithium ion battery. However, the power supply unit 22 may be a replaceable primary battery. The power supply unit 22 is electrically connected to the control unit 28 and supplies electric power.

The blocks in the control unit 28 are implemented in the hardware by any CPU (central processing unit) of a computer, other elements, or mechanical devices, and in software by a computer program or the like. The figure depicts functional blocks implemented by the cooperation of hardware and software. Thus, a person skilled in the art with knowledge of the present specification should appreciate that there are many ways of accomplishing these functional blocks in various forms in accordance with the components of the combination of hardware and software. The same applies to the blocks in FIGS. 4 and 5.

The power supply control unit 50 controls the charging of the power supply unit 22 and transmits information indicating the charging status to the exercise instrument controller 12 via the communication unit 58.

The skin detection unit 52 detects whether or not electrodes are in contact with the skin. The skin detection unit 52 detects the value of resistance between the first electrode group 31 and the second electrode group 32 and the value of resistance between the third electrode group 33 and the fourth electrode group 34. The skin detection unit 52 detects that the electrodes are in contact with the skin when a detected value of resistance is less than a threshold value and detects that the electrodes are not in contact with the skin when the detected value of resistance is the threshold value or more.

Upon detection that the electrodes are in contact with the skin conducted by the skin detection unit 52, the electrostimulation control unit 54 applies voltage between the electrodes for a predetermined operation time (for example, 23 minutes) and at a predetermined cycle (for example, a cycle where the frequency becomes 20 Hz). In other words, electrostimulation is applied to the abdominal muscle and flank of the user. The setting unit 56 receives manipulation input for the plus button 20a and the minus button 20b arranged one above the other and increases or decreases the value of set voltage that is applied to the electrostimulation control unit 54. In other words, the setting unit 56 increases the value of the set voltage every time the user presses the plus button 20a and decreases the value of the set voltage every time the user presses the minus button 20b. The value of the set voltage can be set to, for example, any value for the intensity in the increments of twenty levels. The setting unit 56 further receives manipulation input for the abdominal muscle designation button 20c and the flank designation button 20d arranged on the left and right and determines whether to manipulate any of the values of the set voltage for the abdominal muscle portion 21a and the left and right flank portions 21b and 21c. The user adjusts the value of the set voltage by the plus button 20a and the minus button 20b after pressing down the abdominal muscle designation button 20c when the user wants to manipulate the value of the set voltage for the abdominal muscle. The user adjusts the value of the set voltage by the plus button 20a and the minus button 20b after pressing down the flank designation button 20d when the user wants to manipulate the value of the set voltage for the flank.

The communication unit 58 receives information regarding set voltage from the exercise instrument controller 12 via short-distance wireless communication and transmits the information to the setting unit 56. When the communication unit 58 receives the information regarding the set voltage from the exercise instrument controller 12 or information indicating to increase or decrease the value of the set voltage, the setting unit 56 increases or decreases the value of the set voltage based on the information that is received. By applying voltage between the electrodes at the new value of the set voltage every time the value of the set voltage is increased or decreased, the electrostimulation control unit 54 allows the user to feel and check the new value of the set voltage, that is, the intensity of exercise. The communication unit 58 also increases or decreases the value of the set voltage if the communication unit 58 receives instruction to increase or decrease the intensity of exercise from the exercise instrument controller 12 even during exercise, that is, during the application of voltage. Even if the communication unit 58 receives instruction to increase or decrease the intensity of exercise from devices other than the exercise instrument controller 12 to which the communication unit 58 is connected, the communication unit 58 ignores the instruction and does not follow instruction to increase or decrease the intensity of exercise from any other devices. This is for the purpose of preventing those other than the user from freely increasing or decreasing the value of the voltage. The communication unit 58 may transmit, to the exercise instrument controller 12, information indicating the status of voltage application by the electrostimulation control unit 54, that is, information indicating the status of the execution of exercise.

Figure 4:
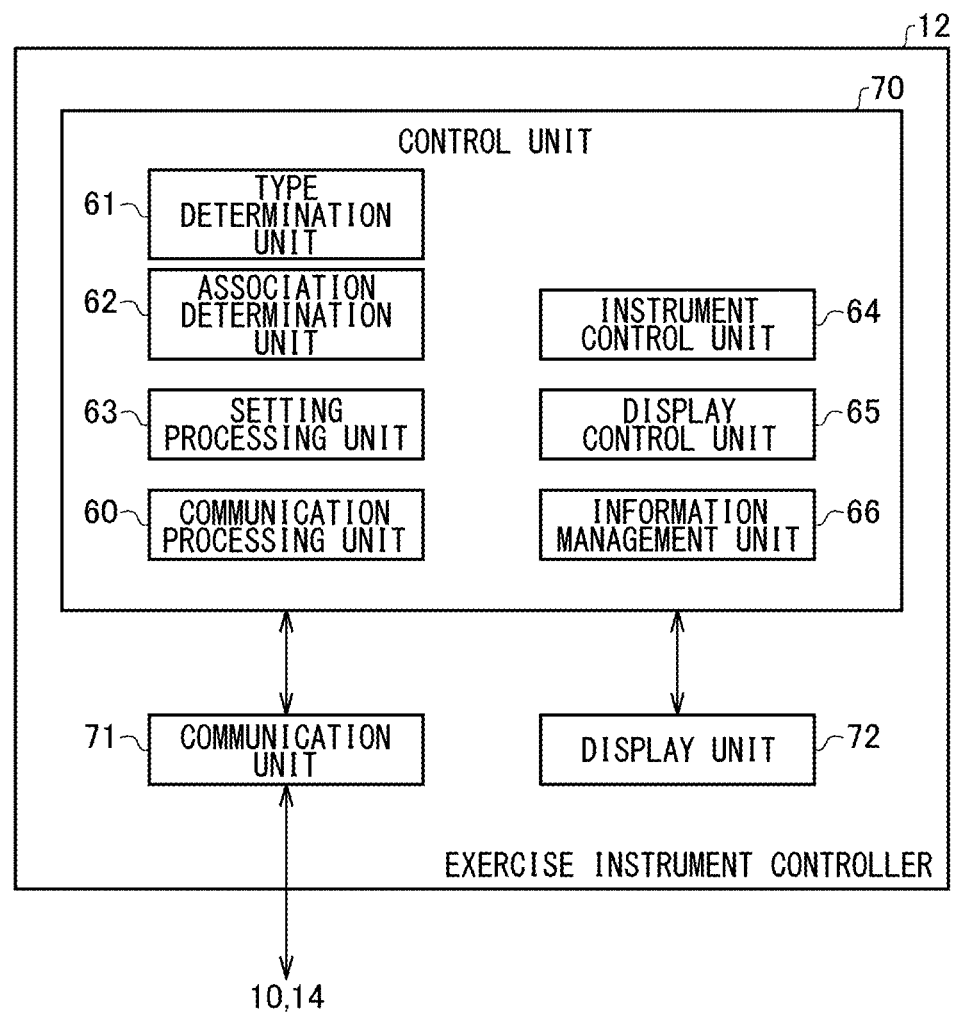
FIG. 4 is a functional block diagram showing functional features of an exercise instrument controller.

<Exercise instrument controller> FIG. 4 is a functional block diagram showing functional features of the exercise instrument controller 12. The exercise instrument controller 12 includes a control unit 70, a communication unit 71, and a display unit 72. The control unit 70 includes a communication processing unit 60, a type determination unit 61, an association determination unit 62, a setting processing unit 63, an instrument control unit 64, a display control unit 65, and an information management unit 66.

The communication unit 71 transmits and/or receives information by short-distance wireless communication to/from the muscle electrostimulation device 10 and transmits and/or receives information via a communication means such a mobile phone communication network or wireless LAN to/from the information management server 14. The control unit 70 transmits and/or receives information via the communication unit 71 to/from the muscle electrostimulation device 10 and the information management server 14. The display unit 72 is a touch-panel display device such as a liquid crystal panel and an OLED panel and receives manipulation input from the user.

The communication processing unit 60 transmits and/or receives information via the communication unit 71 to/from the muscle electrostimulation device 10. The information received by the communication processing unit 60 from each of the plurality of types of exercise instruments has different contents for each type of the exercise instruments. For example, the information received from each exercise instrument includes identification information that indicates the type of the exercise instrument and the type of the exercise. The information received from each exercise instrument may include individual identification information or a unique network address (MAC address) that is used for user registration or individual management.

The type determination unit 61 specifies, from among a plurality of types, the type of exercise for which an exercise instrument is used based on the information that has been received. The type determination unit 61 stores, for each type of the exercise instruments, types of exercise that can be done using the type of an exercise instrument in advance. The type determination unit 61 stores exercise instrument names or the types of exercise such as, for example, "Abs+Waist", "Abs", "Arm", "Leg", and "Body" in advance. The type determination unit 61 specifies the type of exercise by specifying the type of exercise instrument based on the information that is received. There is a case where, once an exercise instrument or the type of exercise is specified as in "Abs+Waist" and "Abs", a body part on which the instrument is used is unambiguously determined just like "abdominal muscle+flank" and "abdominal muscle". However, in other exercise instruments, body parts on which the exercise instruments are used are not always determined unambiguously. For example, whether an exercise instrument "Arm" is used for the right arm or the left arm and whether the exercise instrument is used for the front side or the back side of an arm cannot be determined without specification by the user. Similarly, whether an exercise instrument "Leg" is used for the right leg or the left leg and whether the exercise instrument is used for the front side or the back side of a leg cannot be determined without specification by the user. Since an exercise instrument "Body" can be used for any of the flanks, the arms, and the legs, a body part for which the exercise instrument is used cannot be determined without specification by the user. Accordingly, the specification of a body part on which an exercise instrument is used is performed as follows based on the type of the exercise instrument or the type of exercise.

Based on respective types of exercise specified for one or a plurality of exercise instruments, the association determination unit 62 specifies the association of a plurality of body parts respectively with different exercise instruments. The association determination unit 62 stores in advance, for each type of exercise, one or more body parts that can be exercised by the type. When there are a plurality of body parts that can be exercised by the type of exercise, that is, when an exercise instrument that requires specification of a body part is worn, the association determination unit 62 specifies the association of any one of the body parts with the exercise instrument based on manipulation input at the display unit 72 by the user.

For example, for a type of exercise "Abs+Waist", a body part "abdominal muscle+flank" is associated in advance, and no specification of a body part by the user is necessary since this is the only option. Similarly, for a type of exercise "Abs", a body part "abdominal muscle" is associated in advance as the only option, and no specification of a body part by the user is thus necessary. On the other hand, for a type of exercise "Arm", four body parts, "front side of the right arm", "back side of the right arm", "front side of the left arm", and "back side of the left arm", are associated, and some sort of specification is necessary. For a type of exercise "Leg", four body parts, "front side of the right leg", "back side of the right leg", "front side of the left leg", and "back side of the left leg", are associated, and some sort of specification is necessary. For a type of exercise "Body", six body parts, "right arm", "left arm", "right flank", "left flank", "right leg", and "left leg", are associated, and some sort of specification is necessary.

The association determination unit 62 stores, in advance, a prohibition standard defining a combination of exercise instruments whose use on a single body part or on related body parts is considered to be excessive use and determines whether the use on a body part that can be exercised according to a specified type is considered to be the excessive use defined in the prohibition standard. Regarding a single body part, for example, a body part such as "abdominal muscle" on which only one exercise instrument can be worn at a time, wearing of a plurality of exercise instruments on such a body part at a time is avoided by the prohibition standard. Regarding related body parts, for example, body parts such as "arms" that can be physically restraining when wearing a plurality of exercise instruments at a time, wearing of a plurality of exercise instruments on such body parts at a time is also avoided by the prohibition standard. This is for the purpose of avoiding the wearing of exercise instruments on both arms that makes the manipulation difficult. When the association determination unit 62 determines that the use is considered to be excessive use under the prohibition standard, the connection of an exercise instrument that causes such excessive use is cancelled or avoided by the instrument control unit 64 and the communication processing unit 60, and a notification indicating that the use falls or can fall under the prohibition standard is displayed on the display unit 72.

The setting processing unit 63 sets the operation detail of an exercise instrument based on manipulation input to the display unit 72 by the user. The setting processing unit 63 can set different operation details respectively for a plurality of body parts. The setting processing unit 63 sets, as an operation detail, the intensity of electrostimulation applied by the muscle electrostimulation device, in other words, employs a value of voltage for any one of the twenty levels.

Based on the association between the body part and the exercise instrument that has been specified and on the operation detail that has been set, the instrument control unit 64 controls, by transmitting information indicating the operation detail to each exercise instrument via the communication unit 71, exercise using the exercise instrument. For example, the instrument control unit 64 controls the muscle electrostimulation device 10 by transmitting an exercise start signal, a pause signal, an end signal, a voltage value signal, or the like to the muscle electrostimulation device 10. On the other hand, in order to reduce the battery consumption caused by communication in the muscle electrostimulation device 10, minimization of the communication is preferable design-wise. For example, the voltage value set for the muscle electrostimulation device 10 is stored in the information management unit 66, and information regarding the voltage value is not acquired from the muscle electrostimulation device 10. Further, without transmitting or receiving an exercise end signal, an exercise program may be determined to have been ended after a predetermined period of time.

The display control unit 65 controls a screen display regarding the association between a body part and an exercise instrument, an operation detail, and an exercising status. The display control unit 65 displays an image of a human body model and displays an image dynamically showing the movement of a muscle being exercised on a screen in accordance with the control status of the exercise instrument. The screen display will be described in detail later.

The information management unit 66 stores registration and attribute information of the user, exercise result information, and the like. As the registration and attribute information of the user, for example, information such as email address, password, nickname, birth date, height, weight, sex, and the like is stored. As a result of exercise for each body part, the information management unit 66 determines the amount of exercise based on an operation detail that is set and performed for each body part using a coefficient for each body part and records a cumulative exercise amount. The information management unit 66 may store a coefficient according to an average muscle or electrode area for each body part in advance and calculate the product of a voltage value, an application time, and a coefficient as the amount of single exercise. The amount of exercise may be displayed using, for example, a unique unit such as "mp". The information management unit 66 accumulates the amount of exercise that is calculated and stores the amount of exercise that has been accumulated as the cumulative exercise amount.

Figure 5:
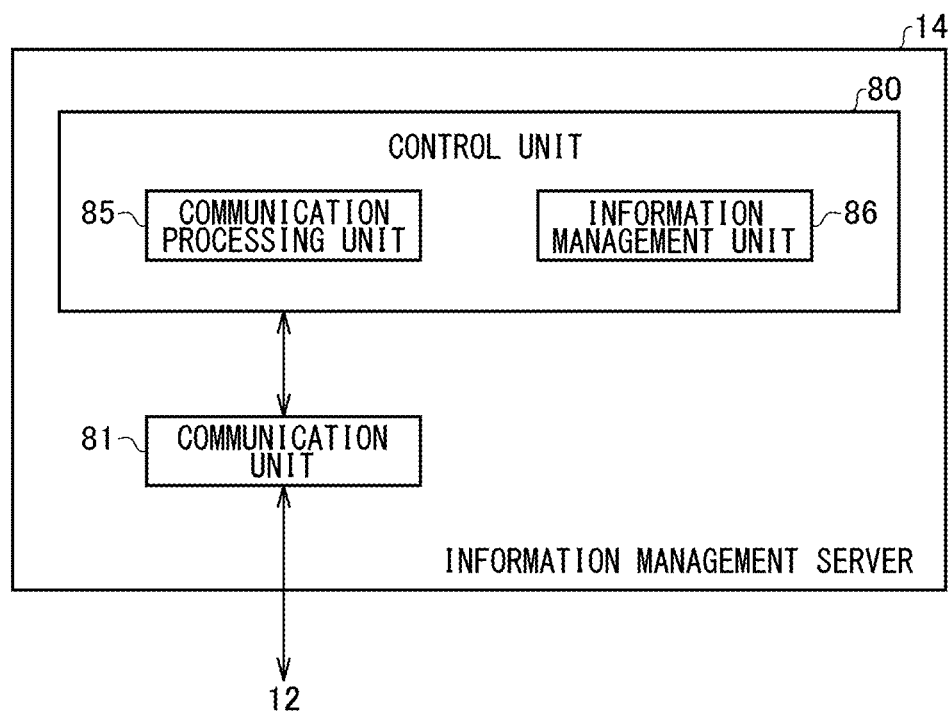
FIG. 5 is a functional block diagram showing functional features of an information management server.

FIG. 5 is a functional block diagram showing functional features of the information management server 14. The information management server 14 includes a control unit 80 and a communication unit 81. The control unit 80 accumulates and manages information received from each of a plurality of exercise instrument controllers 12. The communication unit 81 transmits and/or receives information to/from each of the plurality of exercise instrument controllers 12 via a communication means such as a mobile phone communication network or wireless LAN.

The control unit 80 includes a communication processing unit 85 and an information management unit 86. The communication processing unit 85 transmits and/or receives information to/from the plurality of exercise instrument controllers 12 via the communication unit 81. The information management unit 86 accumulates and manages information received from the plurality of exercise instrument controllers 12. The information received from the exercise instrument controllers 12 is, for example, setting information for the muscle electrostimulation device 10 and data for an exercise result for each of the exercise instrument controllers 12. The information management unit 86 stores an exercise control program and distributes, when there is an update for the exercise control program, a program of a new version to the exercise instrument controllers 12 via the communication unit 81.

An explanation will be given on the premise that the exercise instrument control system 100 in the present embodiment includes the information management server 14. However, an exercise instrument control system 100 that does not include the information management server 14 can be also realized in another embodiment. In that case, setting information and information for an exercise result for each of the exercise instrument controllers 12 are mainly stored in a memory means in the exercise instrument controllers 12.

An explanation will be given appropriately using exemplary screens in the following regarding the operation of an exercise instrument control program in an exercise instrument controller 12 and a step (module) for controlling a muscle electrostimulation device 10.

<Starting program> The exercise instrument controller 12 controls the muscle electrostimulation device 10 by means of each function being fulfilled by the exercise instrument control program. First, the display control unit 65 displays a launch screen (not shown) that is also called "splash screen". At the time of the initial starting, the display control unit 65 displays a screen allowing for the selection of any one of (1) account registration, (2) login (for a user who already has an account), and (3) start training without registration. When the user selects (1) account registration, the setting processing unit 63 allows the user to enter information such as email address, password, nickname, birth date, height, weight, sex, and the like, transmits the information that has been entered to the information management server 14 via the communication unit 71, and also stores the information in the information management unit 66. The setting processing unit 63 starts a login status directly in the case of the account registration. If the status is not a login status at the time the program is started, the display control unit 65 also displays a screen that allow for the selection of any one of the options (1) through (3). When the user selects (2) login, the setting processing unit 63 performs a login process based on the email address and the password that have been entered. When the user selects (3) start training without registration, the instrument control unit 64 starts setting or controlling the muscle electrostimulation device 10 without performing account registration or a login process. If the user has already logged in at the time the program is started, the display control unit 65 does not display the above screen. If the user has not already logged in, the display control unit 65 displays the above screen at the time the program is started. The above items necessary for the account registration are merely shown as examples. Alternatively, setting may be done by allowing the user to enter, for example, a purpose for exercise such as muscle enhancement, weight loss, muscle endurance enhancement, or the like. For example, an association relationship between information such as a purpose of exercise, age, sex, height, weight, and the like and an appropriate program may be stored in advance in a table, and a program or advice according to the attribute or situation of the user may be presented.

On the other hand, during the display or after the display of the launch screen, the setting processing unit 63 and the communication processing unit 60 communicate with the information management server 14 via the communication unit 71, check whether or not there is a version update for the exercise instrument control program or for a program module included in the program, and download the update, if any, so as to update the version. During the update, the display control unit 65 displays a screen indicating that the update is being performed (not shown). In the case of the first launch after the update, the display control unit 65 displays the details of the update on a screen (not shown). The display control unit 65 then displays a home screen. In addition, the display control unit 65 displays, as a menu screen, links for FAQs (frequently asked questions), terms of use, privacy policy, used libraries, inquiries, log-out, manuals, etc.

<Start>

Figure 6B:
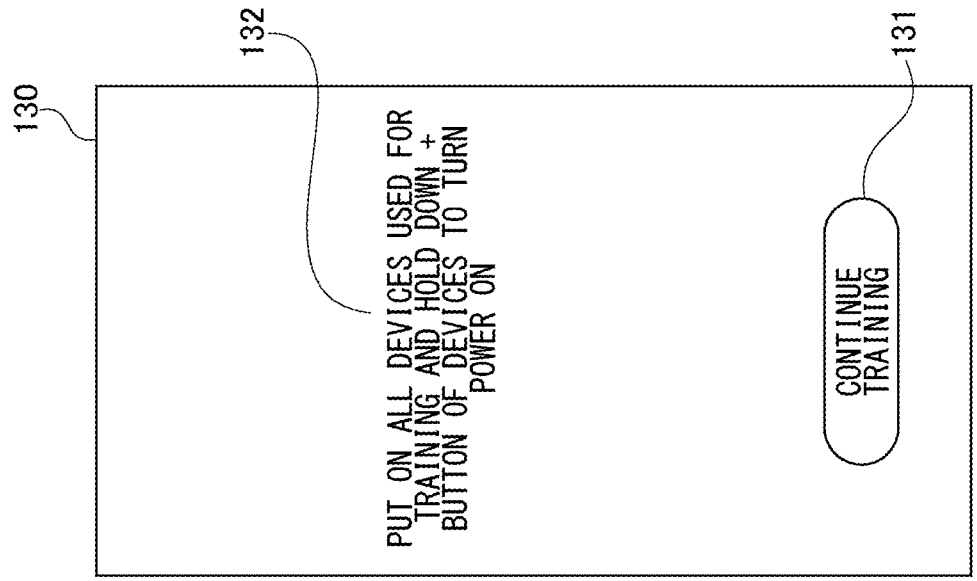
FIGS. 6A-6B are diagrams schematically showing a home screen and a start screen.
Figure 6A:
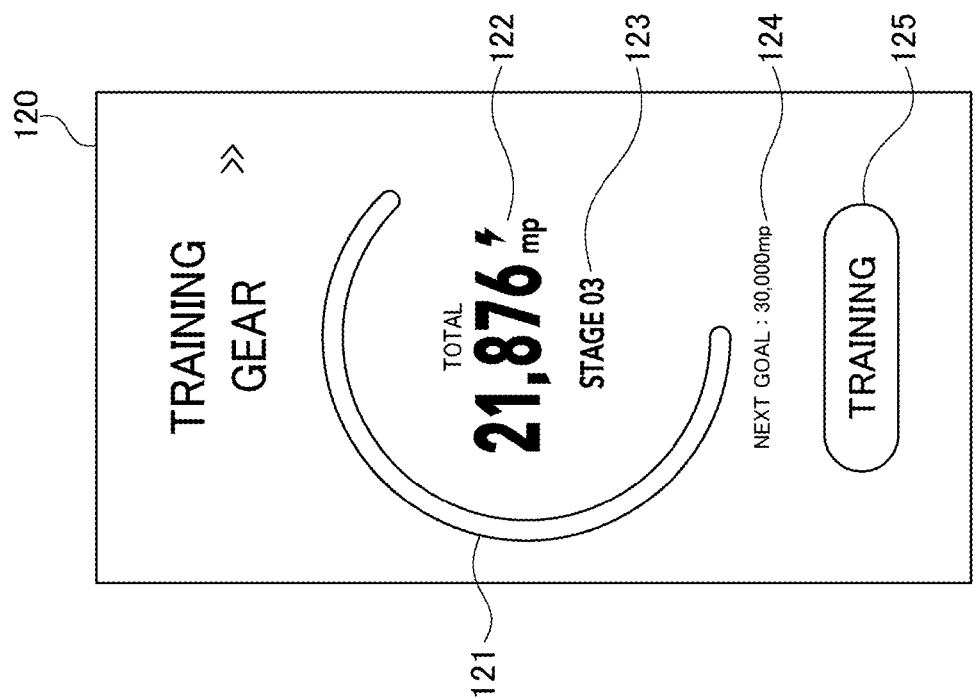

FIGS. 6A-6B schematically show a home screen and a start screen. On a home screen 120 in FIG. 6A, an exercise amount meter 121, a cumulative exercise amount display 122, a stage display 123, a target value display 124, and a start button 125 are displayed. In the present embodiment, the information management unit 66 manages the progress of exercise done by the user in the form of the cumulative exercise amount and manages which level the user belongs to based on the cumulative exercise amount. As levels for exercise, the information management unit 66 stores the criteria for a plurality of levels in advance and manages which level the current cumulative exercise amount belongs to using a "stage" number. The stage number increments, for example, from 1 to 10. In the home screen 120, the exercise amount meter 121 is a circular meter display that shows the ratio of the current cumulative exercise amount at the current stage. Once the circular meter goes around the circumference, the upper limit for a reference value for the cumulative exercise amount for that stage is reached, and the stage number goes up by one. The cumulative exercise amount display 122 shows the current cumulative exercise amount. The stage display 123 shows the current stage number. The target value display 124 shows the upper limit for the cumulative exercise amount that serves as a reference for going up to a next stage. The start button 125 is a button that triggers the start of the exercise. When the user pushes the start button 125 (also referred to as "tapping", which is touch panel pushing manipulation), the screen is changed to the start screen 130 so as to start the controlling of the muscle electrostimulation device 10.

The start screen 130 of FIG. 6B is a screen for explaining initial steps when starting the controlling of the muscle electrostimulation device 10. An explanation 132 is an explanation that prompts the user to put one or a plurality of muscle electrostimulation devices, which are exercise instruments used for exercise, on the user's body and to hold down (e.g., two seconds or more) a "+ button", which is a power activation button of the muscle electrostimulation device 10 so as to turn the power on (a sleep state may be cancelled instead of turning the power on). A continue button 131 is a button for instructing the continuation of a process for moving to a next step. While the start screen 130 is being displayed, the communication processing unit 60 goes into a connection standby state by short-distance wireless communication and accepts connection with the muscle electrostimulation device 10.

<Instrument Recognition and Type Specification>

The communication processing unit 60 and the setting processing unit 63 continue to be in a connection standby state by short-distance wireless communication for a predetermined period of time and, in the meanwhile, establish connection with one or a plurality of muscle electrostimulation devices 10. For an exercise instrument with no connection history, a pairing process may be performed prior to connection. When the user holds down a plus button 20a of the muscle electrostimulation device 10 and skin is detected while the exercise instrument controller 12 is in a connection standby state, information is transmitted through short-distance wireless communication to the exercise instrument controller 12 from the muscle electrostimulation device 10. This allows for pairing or the establishment of connection.

Figure 7:
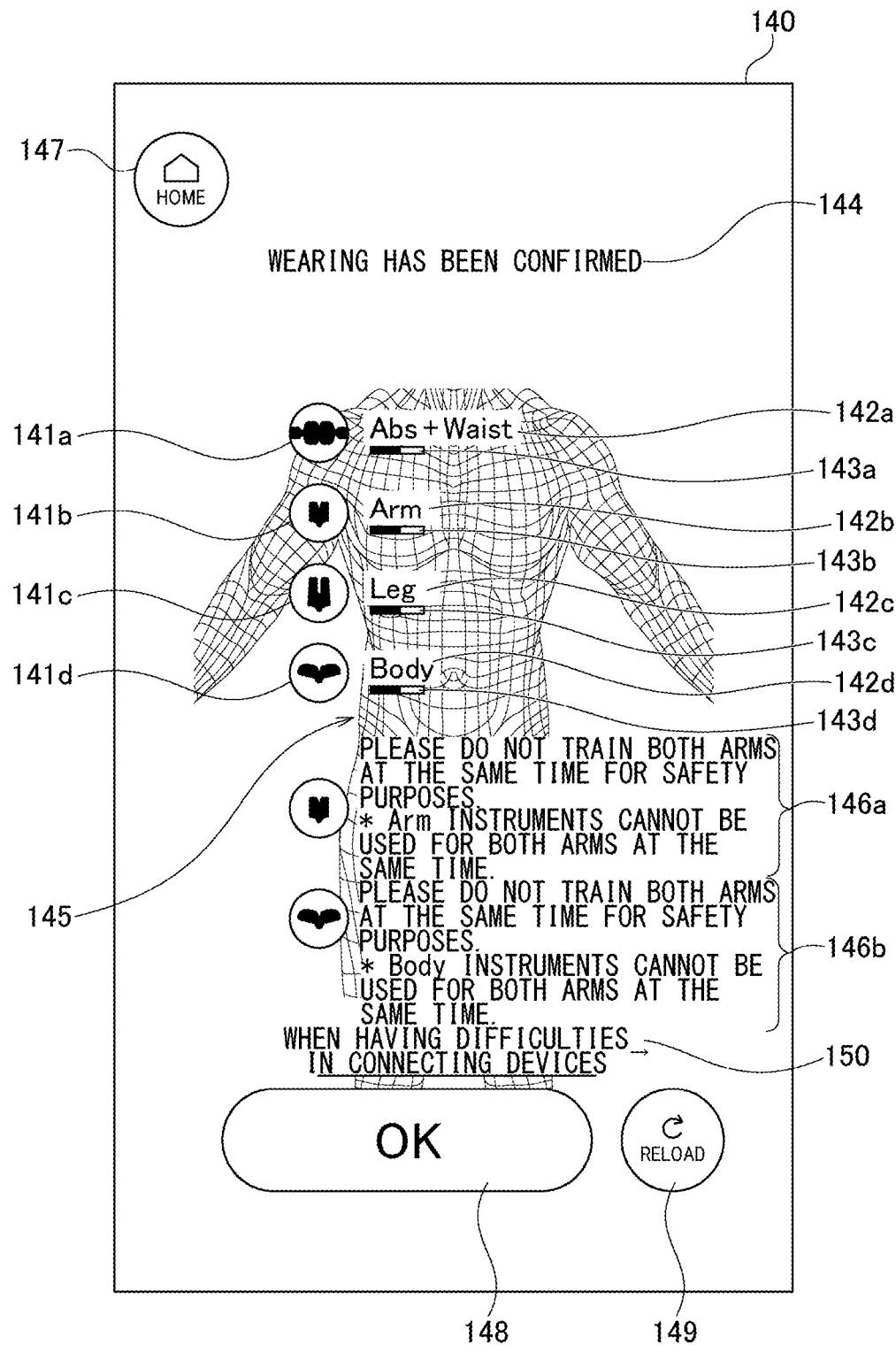
FIG. 7 is a diagram schematically showing a wearing confirmation screen.

FIG. 7 schematically shows a wearing confirmation screen 140. When connection to one or more muscle electrostimulation devices 10 is established, the display control unit 65 displays an explanation showing that the wearing has been confirmed as a connection state display 144 and displays, on the wearing confirmation screen 140, an icon showing a connected exercise instrument, a letter string showing an exercise instrument name or exercise type name, a meter showing an operation state, and an OK button 148. In the present embodiment, up to six exercise instruments can be connected.

Instrument icons 141a to 141d are icons that show the respective types of exercise instruments that have been connected. Instrument names 142a to 142d are letter strings that show the respective names of the exercise instruments that have been connected or the respective names of exercise types. The instrument names 142a to 142d may be names of the exercise instruments or names that show the types of the exercise instruments or may be names that show the both names. Operation state meters 143a to 143d are meters that show the remaining battery capacity of the exercise instruments that have been connected. Information regarding the remaining battery capacity of each exercise instrument is acquired by the communication processing unit 60 from the muscle electrostimulation device 10 via the communication unit 71. A list of the instrument icons 141, the instrument names 142, and the operation state meters 143 is displayed having an image of a human body model 145 as a background. In one variation, the display control unit 65 may display the instrument icons 141, the instrument names 142, and the operation state meters 143 over corresponding body parts of the human body model 145.

Prohibition displays 146a and 146b are explanations that show a situation where the connection of a new exercise instrument can fall under the prohibition standard or explanations that show a situation where an exercise instrument that has been connected falls under excessive use under the prohibition standard. For example, these are explanations such as "Please do not train both arms at the same time for safety purposes" that show that wearing exercise instruments on both arms at the same time falls under the prohibition standard for a safety reason where the manipulation of the muscle electrostimulation device 10 or the exercise instrument controller 12 may become difficult. Further, by listing a specific name of an exercise instrument or an exercise type, which exercise instrument combination falls under the prohibition standard or on which body part wearing of exercise instruments at the same time falls under the prohibition standard is shown. This allows for the ensuring of safety and the ensuring of proper use in terms of the specifications of instruments in doing exercise. A help link 150 is a link for switching to a screen that shows coping methods for when the communication connection with the muscle electrostimulation device 10 cannot be established.

When a predetermined period of time, which is a standby time for communication connection, has passed or when the number of muscle electrostimulation devices 10 whose connection has been established reaches a predetermined upper limit number, the display control unit 65 lights up and displays a reload button 149 (the pushing of the button becomes effective only when the button becomes lit up and displayed). When the pushing of the OK button 148 by the user is detected, the display control unit 65 switches to a next screen. When not even a single exercise instrument is recognized after the predetermined period of time, which is the standby time, has passed, the display control unit 65 lights up and displays the reload button 149 without lighting up and displaying the OK button 148. When the pushing of the reload button 149 by the user is detected, the connection with one or a plurality of muscle electrostimulation devices 10 is started over from the beginning. In other words, the communication processing unit 60 cancels all connection with each exercise instrument once and starts over with the recognition from the beginning. A home button 147 is a button to go back to the home screen 120 of FIG. 6.

<Prohibition Standard>

FIG. 8 schematically shows a prohibition table that sets prohibition standards. The prohibition table includes a connection count by instrument column 160, a total connection count column 161, a disconnecting instrument name column 162, and an explanation column 163. The connection count by instrument column 160 defines prohibited combinations of exercise instrument names and the number of connections. The total connection count column 161 defines the total numbers of connections in the prohibited combinations. The disconnecting instrument name column 162 defines exercise instruments for which the connection should be disconnected when the prohibition applies. The explanation column 163 defines text examples displayed when the prohibition applies. The prohibited combinations include a case where one type of exercise instrument is involved (first column 156), a case where two types of exercise instruments are involved (second column 157), a case where three types of exercise instruments are involved (third column 158), and a case where four types of exercise instruments are involved (four column 159). The first column 156 through the fourth column 159 define combinations that are at least any one of combinations where exercise instruments whose count is more than the number of specific body parts are worn on the body parts and combinations where specific body parts become restrained when exercise instruments whose count is the same as the number of the body parts are worn on the body parts.

As a combination example in the first column 156, "2" the number of exercise instruments worn on an abdominal muscle exceeds one) is listed for "Abs" in the connection count by instrument column 160, the number of connections is listed as "2" in the total connection count column 161, "Abs" is listed in the disconnecting instrument name column 162, and text "* Two or more Abs instruments cannot be used at the same time." is listed in the explanation column 163. In the same way, as a combination example where two "Abs+Waist" instruments are worn on an abdominal muscle, "2" (the number of the instruments worn on the abdominal muscle and flank exceeds one) is listed for "Abs+Waist" in the connection count by instrument column 160, the number of connections is listed as "2" in the total connection count column 161, "Abs+Waist" is listed in the disconnecting instrument name column 162, and text "* Two or more Abs+Waist instruments cannot be used at the same time." is listed in the explanation column 163. As a combination example in the first column 156, "3" (the number of exercise instruments worn on both legs exceeds two) is listed for "Leg" in the connection count by instrument column 160, the number of connections is listed as "3" in the total connection count column 161, "Leg" is listed in the disconnecting instrument name column 162, and text "* Three or more Leg instruments cannot be used at the same time." is listed in the explanation column 163. As a combination example in the first column 156, "6" (whether exercise instruments are worn on both arms or the number of exercise instruments worn on either flanks or legs exceeds two) is listed for "Body" in the connection count by instrument column 160, the number of connections is listed as "6" in the total connection count column 161, "Body" is listed in the disconnecting instrument name column 162, and text "* Six or more Body instruments cannot be used at the same time." is listed in the explanation column 163. As a combination example in the first column 156, "2" (exercise instruments are worn on both arms) is listed for "Arm" in the connection count by instrument column 160, the number of connections is listed as "2" in the total connection count column 161, "Arm" is listed in the disconnecting instrument name column 162, and text "* Please do not train both arms at the same time for safety purposes. Two or more Arm instruments cannot be used at the same time." is listed in the explanation column 163.

As a combination example in the second column 157, "1" is listed for "Abs" and "1" (the number of exercise instruments worn on an abdominal muscle exceeds one) is listed for "Abs+Waist" in the connection count by instrument column 160, the number of connections is listed as "2" in the total connection count column 161, "Abs" is listed in the disconnecting instrument name column 162, and text "* Abs instrument and Abs+Waist instrument cannot be used at the same time." is listed in the explanation column 163. In the same way, "1" is listed for "Abs+Waist" and "4" (whether exercise instruments are worn on both arms or the number of exercise instruments worn on either flanks or legs exceeds two) is listed for "Body" in the connection count by instrument column 160, the number of connections is listed as "5" in the total connection count column 161, "Body" is listed in the disconnecting instrument name column 162, and text "* Exceeding the number of parts that can be trained by the devices that are worn." is listed in the explanation column 163. As another combination example in the second column 157, "1" is listed for "Leg" and "5" (whether exercise instruments are worn on both arms or the number of exercise instruments worn on either flanks or legs exceeds two) is listed for "Body" in the connection count by instrument column 160, the number of connections is listed as "6" in the total connection count column 161, "Body" is listed in the disconnecting instrument name column 162, and text "* Exceeding the number of parts that can be trained by the devices that are worn." is listed in the explanation column 163. In the same way, "2" is listed for "Leg" and "4" (whether exercise instruments are worn on both arms or the number of exercise instruments worn on either flanks or legs exceeds two) is listed for "Body" in the connection count by instrument column 160, the number of connections is listed as "6" in the total connection count column 161, "Body" is listed in the disconnecting instrument name column 162, and text "* Exceeding the number of parts that can be trained by the devices that are worn." is listed in the explanation column 163. As another combination example in the second column 157, "1" is listed for "Arm" and "5" (whether exercise instruments are worn on both arms or the number of exercise instruments worn on either flanks or legs exceeds two) is listed for "Body" in the connection count by instrument column 160, the number of connections is listed as "6" in the total connection count column 161, "Body" is listed in the disconnecting instrument name column 162, and text "* Exceeding the number of parts that can be trained by the devices that are worn." is listed in the explanation column 163.

As a combination example in the third column 158, "1" is listed for "Abs+Waist", "1" is listed for "Arm", and "3" (whether exercise instruments are worn on both arms or the number of exercise instruments worn on either flanks or legs exceeds two) is listed for "Body" in the connection count by instrument column 160, the number of connections is listed as "5" in the total connection count column 161, "Body" is listed in the disconnecting instrument name column 162, and text "* Exceeding the number of parts that can be trained by the devices that are worn." is listed in the explanation column 163. In the same way, "1" is listed for "Abs+Waist", "1" is listed for "Leg", and "3" (whether exercise instruments are worn on both arms or the number of exercise instruments worn on either flanks or legs exceeds two) is listed for "Body" in the connection count by instrument column 160, the number of connections is listed as "5" in the total connection count column 161, "Body" is listed in the disconnecting instrument name column 162, and text "* Exceeding the number of parts that can be trained by the devices that are worn." is listed in the explanation column 163. In the same way, "1" is listed for "Abs+Waist", "2" is listed for "Leg", and "2" (whether exercise instruments are worn on both arms or the number of exercise instruments worn on either flanks or legs exceeds two) is listed for "Body" in the connection count by instrument column 160, the number of connections is listed as "5" in the total connection count column 161, "Body" is listed in the disconnecting instrument name column 162, and text "* Exceeding the number of parts that can be trained by the devices that are worn." is listed in the explanation column 163. In the same way, "1" is listed for "Arm", "1" is listed for "Leg", and "4" (whether exercise instruments are worn on both arms or the number of exercise instruments worn on either flanks or legs exceeds two) is listed for "Body" in the connection count by instrument column 160, the number of connections is listed as "6" in the total connection count column 161, "Body" is listed in the disconnecting instrument name column 162, and text "* Exceeding the number of parts that can be trained by the devices that are worn." is listed in the explanation column 163. In the same way, "1" is listed for "Arm", "2" is listed for "Leg", and "3" (whether exercise instruments are worn on both arms or the number of exercise instruments worn on either flanks or legs exceeds two) is listed for "Body" in the connection count by instrument column 160, the number of connections is listed as "6" in the total connection count column 161, "Body" is listed in the disconnecting instrument name column 162, and text "* Exceeding the number of parts that can be trained by the devices that are worn." is listed in the explanation column 163.

As a combination example in the four column 159, "1" is listed for "Abs+Waist", "1" is listed for "Arm", "1" is listed for "Leg", and "2" (whether exercise instruments are worn on both arms or the number of exercise instruments worn on either flanks or legs exceeds two) is listed for "Body" in the connection count by instrument column 160, the number of connections is listed as "5" in the total connection count column 161, "Body" is listed in the disconnecting instrument name column 162, and text "* Exceeding the number of parts that can be trained by the devices that are worn." is listed in the explanation column 163. In the same way, "1" is listed for "Abs+Waist", "1" is listed for "Arm", "2" is listed for "Leg", and "1" (whether exercise instruments are worn on both arms or the number of exercise instruments worn on either flanks or legs exceeds two) is listed for "Body" in the connection count by instrument column 160, the number of connections is listed as "5" in the total connection count column 161, "Body" is listed in the disconnecting instrument name column 162, and text "* Exceeding the number of parts that can be trained by the devices that are worn." is listed in the explanation column 163.

In the present embodiment, when the prohibition standard applies, an exercise instrument that has been connected first is prioritized, and the connection with an exercise instrument that is recognized later is avoided or cancelled. In a variation, the setting may be overwritten by prioritizing the connection with an exercise instrument that is recognized later and cancelling the connection with an exercise instrument that has been connected first. Alternatively, the user may be allowed to select which one is to be prioritized.

<Part Setting>

Figure 9:
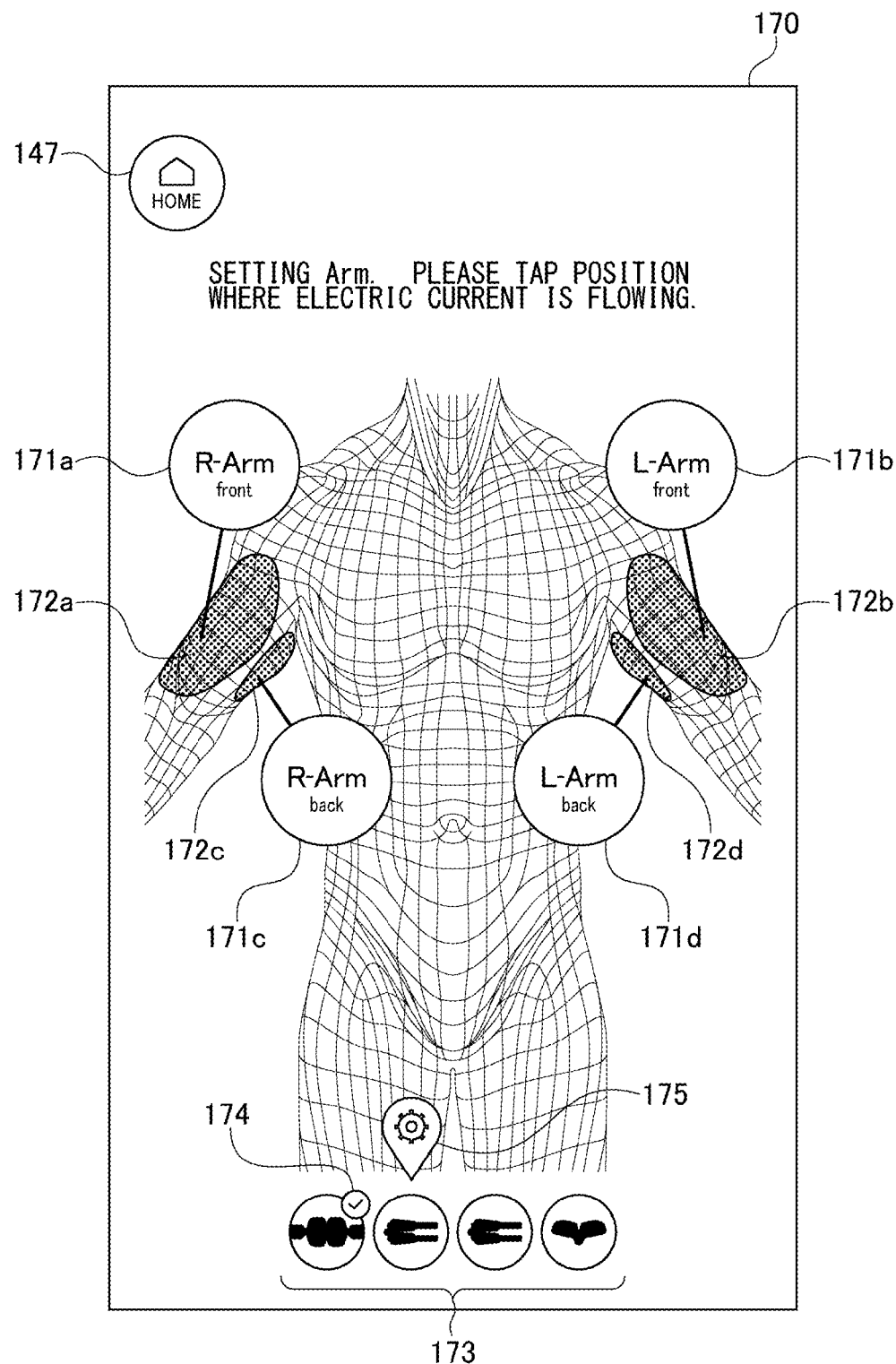
FIG. 9 is a diagram schematically showing an exemplary screen for setting body parts on which exercise instruments are used.

FIG. 9 schematically shows an exemplary screen for setting body parts on which exercise instruments are used. In the example in the figure, on which body part "Arm", i.e., an exercise instrument to be worn on an arm is used is specified. In a part setting screen 170, the user specifies a body part on which the exercise instrument "Arm" is used. In the case of "Arm", the exercise instrument can be worn on any one part of the front side or the back side of the arms. A first part button 171a marked "R-Arm front" meaning the front side of a right arm points to an area 172a, which is the front side of a right arm of the human body model 145. Pushing of the first part button 171a by the user means that "Arm" is specified to be used on the front side of the right arm. A second part button 171b marked "L-Arm front" meaning the front side of a left arm points to an area 172b, which is the front side of a left arm of the human body model 145. Pushing of the second part button 171b by the user means that "Arm" is specified to be used on the front side of the left arm. A third part button 171c marked "R-Arm back" meaning the back side of a right arm points to an area 172c, which is the back side of the right arm of the human body model 145. Pushing of the third part button 171c by the user means that "Arm" is specified to be used on the back side of the right arm. A fourth part button 171d marked "L-Arm back" meaning the back side of a left arm points to an area 172d, which is the back side of the left arm of the human body model 145. Pushing of the fourth part button 171d by the user means that "Arm" is specified to be used on the back side of the left arm. When the user pushes any one of the first through fourth part buttons 171a through 171d, a part setting for "Arm" is ended directly. In order to allow the user to check which individual instrument is the exercise instrument used for the body part when any one of the first through fourth part buttons 171a through 171d is pushed, a weak electric current may be applied to the exercise instrument that corresponds to the body part, or vibration of a vibrator or blinking of an LED lamp inside the exercise instrument may be activated. This is because wearing two or more "Arm" instruments fall under the prohibition standard allowing only one part to be specified. The display control unit 65 displays type icons 173 that show already connected exercise instruments or exercise types side by side on the lower side of the human body model 145, adds a check mark 174 to a type icon 173 for which a body part to be used is already set, and shows a setting process mark 175 showing that the setting process is going on for a type icon that is currently in the process of being set above the type icon 173. Body parts on which the type "Abs" or "Abs+Waist" is worn are fixed, and there is thus no room for the user to specify body parts. Thus, the types "Abs" and "Abs+Waist" are not subject to body part specification in the part setting screen 170. Therefore, as shown by the type icons 173, check marks 174 are added to "Abs" and "Abs+Waist" type icons 173 from the beginning. Also, when all already-connected exercise instruments are those instruments for which body parts on which the instruments are to be worn are fixed (for example, "Abs" and "Abs+Waist"), the display of a screen for specifying body parts such as the one shown in the figure may be skipped. In that case, a screen that shows body parts to be exercised on a human body model in a determined manner may be displayed instead of a part setting screen.

Figure 10:
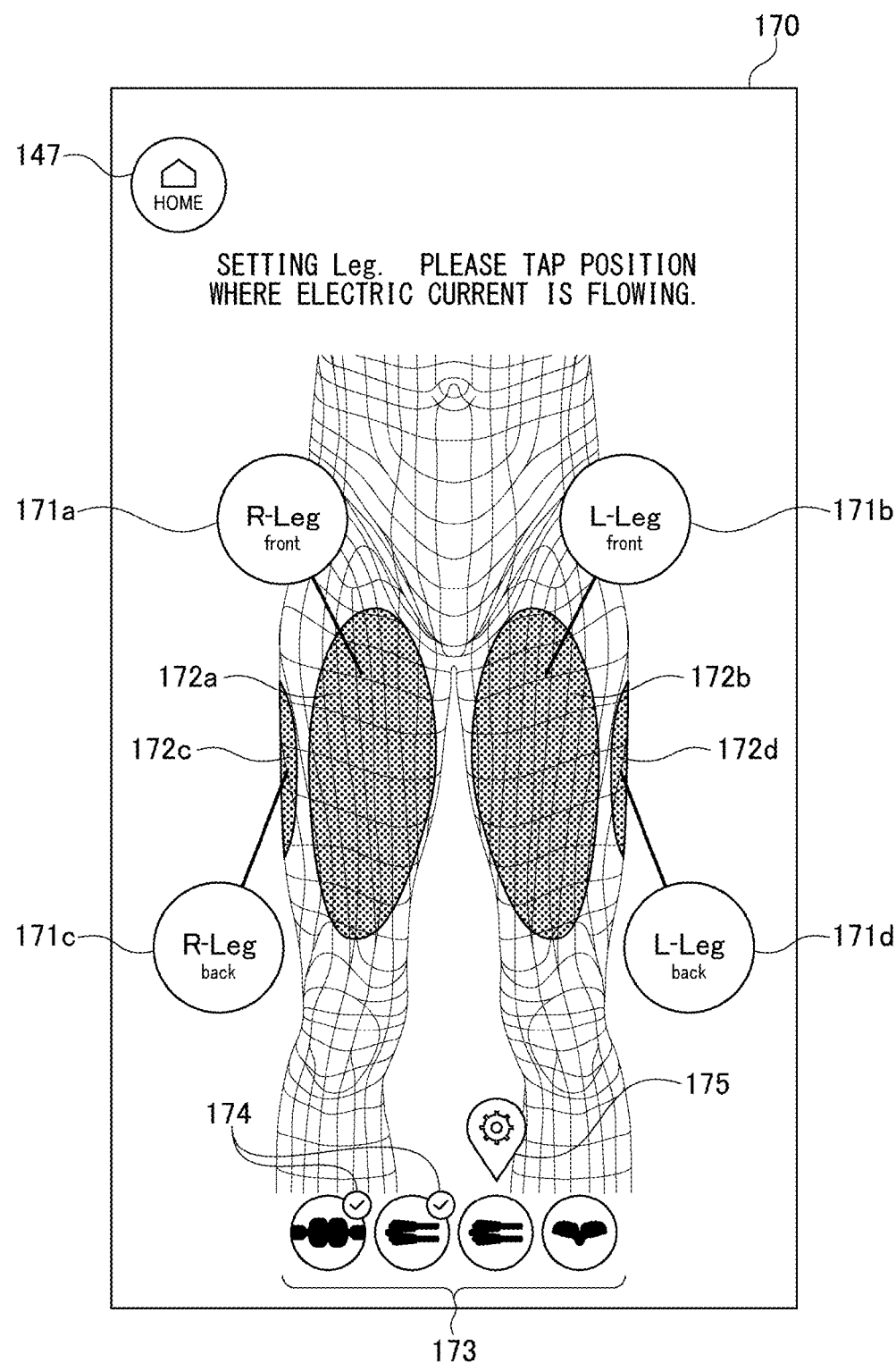
FIG. 10 is a diagram schematically showing a part setting screen for a type "Leg"

FIG. 10 schematically shows a part setting screen for a type "Leg". In a part setting screen 170, the user specifies a body part on which an exercise instrument "Leg" is used. In the example in the figure, on which body part "Leg", i.e., an exercise instrument to be worn on a leg is used is specified. In the case of "Leg", the exercise instrument can be worn on up to two parts: the front side or the back side of a right leg; and the front side or the back side of a left leg. A first part button 171a marked "R-Leg front" meaning the front side of a right leg points to an area 172a, which is the front side of a right leg of the human body model 145. Pushing of the first part button 171a by the user means that "Leg" is specified to be used on the front side of the right leg. A second part button 171b marked "L-Leg front" meaning the front side of a left leg points to an area 172b, which is the front side of a left leg of the human body model 145. Pushing of the second part button 171b by the user means that "Leg" is specified to be used on the front side of the left leg. A third part button 171c marked "R-Leg back" meaning the back side of a right leg points to an area 172c, which is the back side of the right leg of the human body model 145. Pushing of the third part button 171c by the user means that "Leg" is specified to be used on the back side of the right leg. A fourth part button 171d marked "L-Leg back" meaning the back side of a left leg points to an area 172d, which is the back side of the left leg of the human body model 145. Pushing of the fourth part button 171d by the user means that "Leg" is specified to be used on the back side of the left leg. When the user pushes any one of the first through fourth part buttons 171a through 171d, a part setting for "Leg" is ended once. When one more "Leg" is being connected, the display control unit 65 displays the part setting screen 170 of the figure again and, when the first "Leg" is specified to be worn on the right leg, displays only the front side of the left leg and the back side of the left leg as the choices for body parts that can be specified for the second "Leg" so as to allow the user to select either one. When the first "Leg" is specified to be worn on the left leg, the display control unit 65 displays only the front side of the right leg and the back side of the right leg as the choices for body parts that can be specified for the second "Leg" so as to allow the user to select either one. As described, the wearing of the instruments on the front side and the back side of the same leg is avoided.

Figure 11:
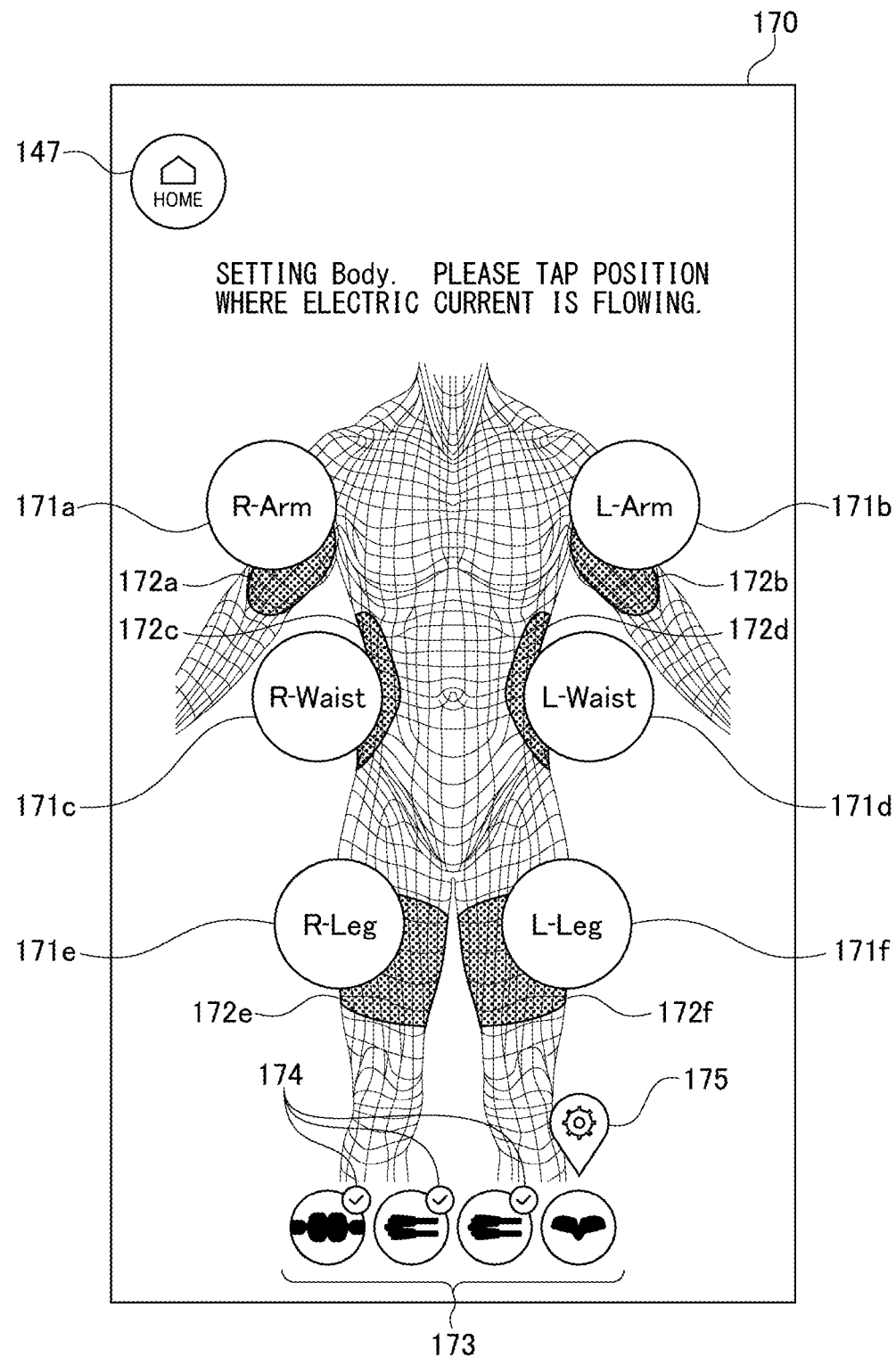
FIG. 11 is a diagram schematically showing a part setting screen for a type "Body"

FIG. 11 schematically shows a part setting screen for a type "Body". In a part setting screen 170, the user specifies a body part on which an exercise instrument "body" is used. In the example in the figure, on which body part "Body", i.e., an exercise instrument to be worn on an arbitrary body part is used is specified. In the case of "Body", different from "Abs", "Abs+Waist", "Arm", and "Leg", parts on which instruments are worn might be the same or the number of instruments that can be worn at the same time might exceed the upper limit for all exercise instruments including "Body". Therefore, after all the specification of parts on which other exercise instruments are worn is finished, a screen for specifying parts on which "Body" is worn is displayed. In a part setting screen 170, if other body parts have not been specified, not even one, at that time, all the body parts other than an abdominal muscle are displayed as choices. In the example of the figure, the front side of both arms, both flanks, and the front side of both legs are displayed as choices. However, if "Abs" or "Abs+Waist" is connected, the both flanks are not displayed as choices. If a part on which "Arm" is worn has already been specified, the both arms are not displayed as choices. If a part on which "Leg" is worn has already been specified, a leg on the side that has been specified is not displayed as a choice. As a variation, the front side and the back side of the both arms, the abdominal muscle, and the front side and the back side of the both legs may be used as choices.

A first part button 171a marked "R-Arm" meaning a right arm points to an area 172a, which is a right arm of the human body model 145. Pushing of the first part button 171a by the user means that "Body" is specified to be used on the right arm. A second part button 171b marked "L-Arm" meaning a left arm points to an area 172b, which is a left arm of the human body model 145. Pushing of the second part button 171b by the user means that "Body" is specified to be used on the left arm. A third part button 171c marked "R-Waist" meaning a right flank points to an area 172c, which is a right flank of the human body model 145. Pushing of the third part button 171c by the user means that "Body" is specified to be used on the right flank. A fourth part button 171d marked "L-Waist" meaning a left flank points to an area 172d, which is a left flank of the human body model 145. Pushing of the fourth part button 171d by the user means that "Body" is specified to be used on the left flank. A fifth part button 171e marked "R-Leg" meaning a right leg points to an area 172e, which is a right leg of the human body model 145. Pushing of the fifth part button 171e by the user means that "Body" is specified to be used on the right leg. A sixth part button 171f marked "L-Leg" meaning a left leg points to an area 172f, which is a left leg of the human body model 145. Pushing of the sixth part button 171f by the user means that "Body" is specified to be used on the left leg. When the user pushes any one of the first through sixth part buttons 171a through 171f, a part setting for "Body" is ended once. When another "Body" is being connected, the display control unit 65 displays the part setting screen 170 of the figure for the number of instruments that are being connected and displays, as choices for body parts that can be specified, only body parts that have not been selected and that do not fall under the prohibition standard so as to allow the user to select any one of the body parts.

FIGS. 12A-12B schematically show an intensity setting screen. Of body parts that have already been specified at this point, for those parts for which there is a record for setting intensity using an exercise instrument in the past, intensity that is the same as that of the last time is automatically set based on the record that is recorded in the information management unit 66. On the contrary, for body parts for which there is no intensity record, that is, body parts for which there is no record of using an exercise instrument in the past, the display control unit 65 displays an intensity setting screen 180 of the FIG. 12A and allows the user to set the intensity for those body parts. In the intensity setting screen 180, an intensity meter 181 shows the intensity in the format of a circular meter and shows the intensity of which level out of twenty voltage levels the intensity of electricity applied to an abdominal muscle is set to in the example of the figure. In the figure, a level "12" is shown. When the user pushes a plus button 182, the intensity level goes up by one, and, when the user pushes a minus button 183, the intensity level goes down by one. The plus button 182 functions the same way as a plus button 20a in a muscle electrostimulation device 10, and the minus button 183 functions the same way as a minus button 20b in a muscle electrostimulation device 10. Every time the user pushes the plus button 182 or the minus button 183, electricity is applied to the abdominal muscle at intensity at a level incremented or decremented by one, and the user adjusts the intensity of the electricity while feeling the intensity and sets the intensity to be desired intensity. When the user pushes an OK button 184, the screen switches to an intensity setting screen for other body parts or to an intensity confirmation screen if the intensity setting has already been finished for all body parts. The display control unit 65 repeats the intensity setting in the intensity setting screen 180 of the FIG. 12A for the number of body parts without a record of intensity setting out of body parts that have been specified.

An intensity confirmation screen 185 of FIG. 12B is a screen to be displayed when the intensity setting has been done for all the body parts that have been specified as parts on which exercise instruments are used this time. In the intensity confirmation screen 185, part buttons 186 showing the name of a part and an intensity setting for each body part are displayed at respective body parts on the human body model 145. When the user pushes any one of part buttons 186a through 186f, an intensity setting screen 180 such as the one shown in FIG. 12A is displayed for adjusting or resetting the intensity for a corresponding body part, allowing the intensity to be adjusted. When the user pushes a start button 187, the training is started.

As described above, the last intensity is set automatically for body parts with an exercise record. However, as a variation, the user may set the intensity every time, or the optimal value may be automatically set according to an exercise program or an exercise record. A default value for the intensity for a body part used for the first time is set in advance. The default value may be the minimum intensity (for example, "1") in order to prevent a high intensity voltage to be applied abruptly.

FIGS. 13A-13B schematically show an exemplary screen displayed during exercise. The display control unit 65 displays an exercising screen 190 such as the one shown in FIG. 13A during the training is performed using an exercise instrument. In the exercising screen 190, the movement of a body part that is exercised by electrostimulation is displayed by a video image also called a visualizer that visually expresses the movement dynamically using an image of the human body model 145. The visualizer expresses the movement of a muscle in synchronization with the timing of the movement of the muscle caused by the electrostimulation. When a plurality of body parts are exercised at the same time, the display control unit 65 switches screens such that all the body parts are displayed in order each for a predetermined period of time, for example, displaying the exercise of any of the body parts on an exercising screen 190 for a predetermined period of time and then switching the screen to an exercising screen 190 displaying the exercise of another body part. On an exercising screen 190, as an exercise execution time, the amount of time defined for an exercise program, e.g., "23 minutes", and an elapsed time are combined and displayed by numerical values such as those of a time display 191 and in the format of a circular meter such as a time meter 192, in addition to the visualizer. On a part of the screen, a pause button 193 is displayed. When the user pushes the pause button 193, the progress of the exercise is temporarily stopped, and the instrument control unit 64 temporarily stops voltage application, and the display control unit 65 temporarily stops the time display 191 and the progress of the time meter 192. In the case of temporary stopping, when the user pushes a button such as "Continue training." on a screen (not shown), the voltage application and the time progress are resumed, and, when the user pushes a button such as "Cancel training.", the voltage application and the time progress are ended. If a predetermined period of time, for example, ten minutes has passed during the temporary stopping, the voltage application and the time progress are ended being considered as time-out. Although not displayed in the example of the figure, the numerical value of the exercise amount may be displayed in such a manner that the numerical value is increased in real time in accordance with the progress of the exercise.

When the user pushes any part of the exercising screen 190, the screen is switched to an intensity confirmation screen 185 such as the one shown in FIG. 13B. The intensity confirmation screen 185 is a screen that basically has the same function as that of the intensity confirmation screen 185 of FIG. 12B, and, even during the exercise, if the user pushes a part button 186 of any body part, the screen can be switched to the intensity setting screen 180 of FIG. 12A so as to adjust the intensity. Every time the user pushes the plus button 182 or the minus button 183 of the intensity setting screen 180, the instrument control unit 64 increases or decreases the voltage level in real time. When the amount of time for the training reaches a predetermined period of time, for example, 23 minutes, the instrument control unit 64 ends the voltage application, and the display control unit 65 ends the progress of time and switches the screen to an end screen. When a program other than the exercise instrument control program that operates in the exercise instrument controller 12 becomes active, screens shown during the exercise such as an exercising screen 190, an intensity confirmation screen 185, an intensity setting screen 180, and the like are turned into an inactive state. If the exercise is ended while the exercise instrument control program is still in an inactive state, the display control unit 65 stands by while keeping the end screen inactive and changes the screen to the next screen after the program becomes active. If the end screen is in an active state, the display control unit 65 changes the screen to the next screen.

Figure 14A:
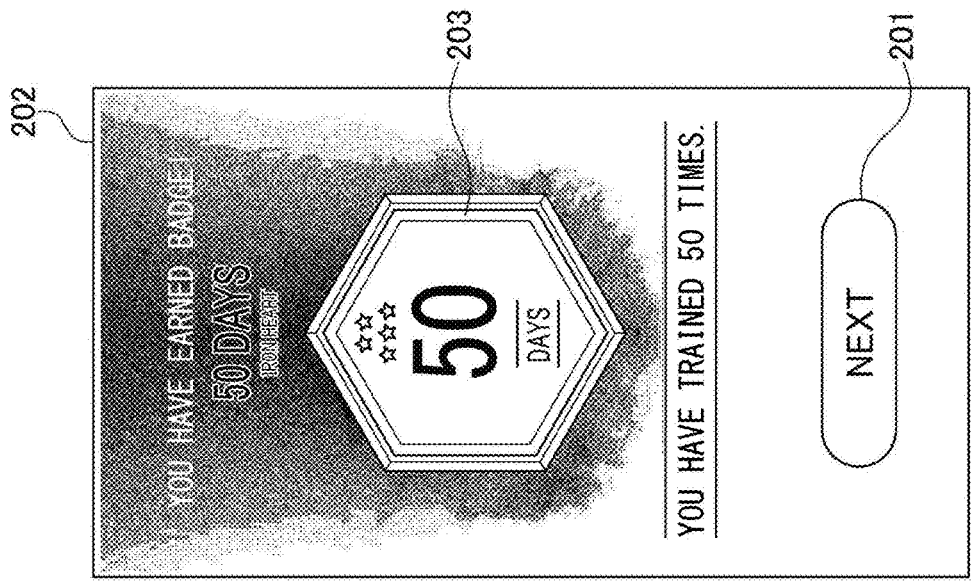
FIGS. 14A-14B are diagrams schematically showing an exemplary screen displaying results.
Figure 14B:
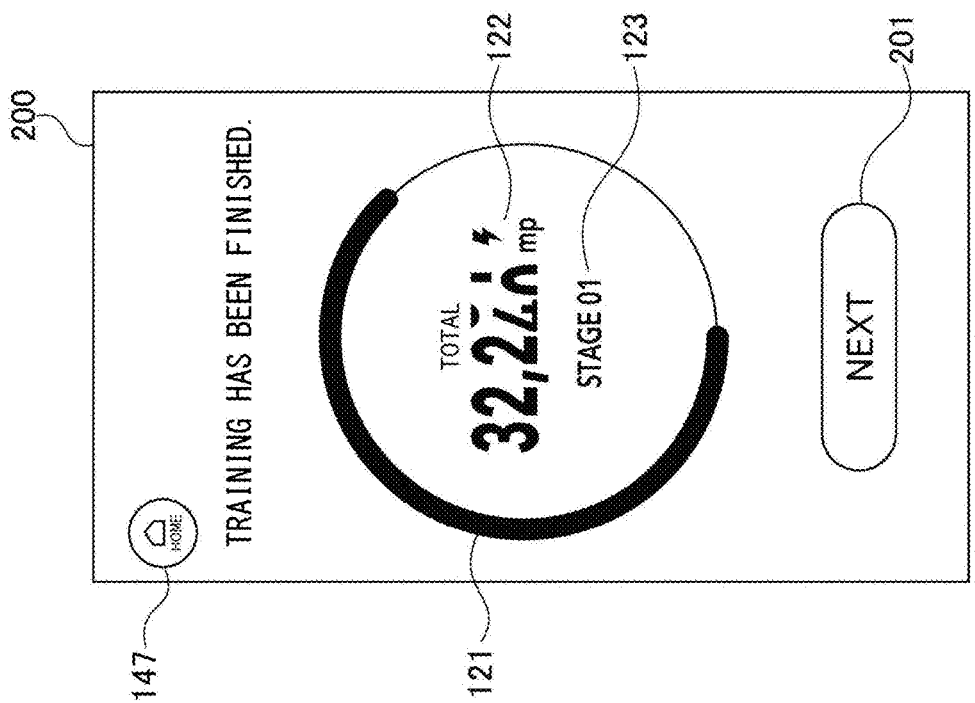

FIGS. 14A-14B schematically show an exemplary screen displaying results. In an exercise amount display screen 200 shown in FIG. 14A, as a result of the exercise, a situation where the performed exercise amount is added to a cumulative exercise amount is displayed by an increase in the numerical value in a cumulative exercise amount display 122 and an increase in an exercise amount meter 121. When the cumulative exercise amount exceeds a predetermined value, a stage number in a stage display 123 is increased. When the user pushes a continue button 201, the display control unit 65 switches the screen to the next screen.

When the cumulative exercise amount or the exercise count reaches predetermined badge acquisition criteria, the display control unit 65 displays a badge 203 acquired by the user and text stating, e.g., "Trained total of 50 times.", which is the acquisition criteria for the badge 203, on a badge screen 202 shown in FIG. 14B. In addition, when the cumulative exercise amount reaches a predetermined value, the display control unit 65 displays advice from a specialist (not shown). As the advice, the display control unit 65 displays different advice according to user's attributes, the purpose of the exercise, the cumulative exercise amount, etc.

Figure 15:
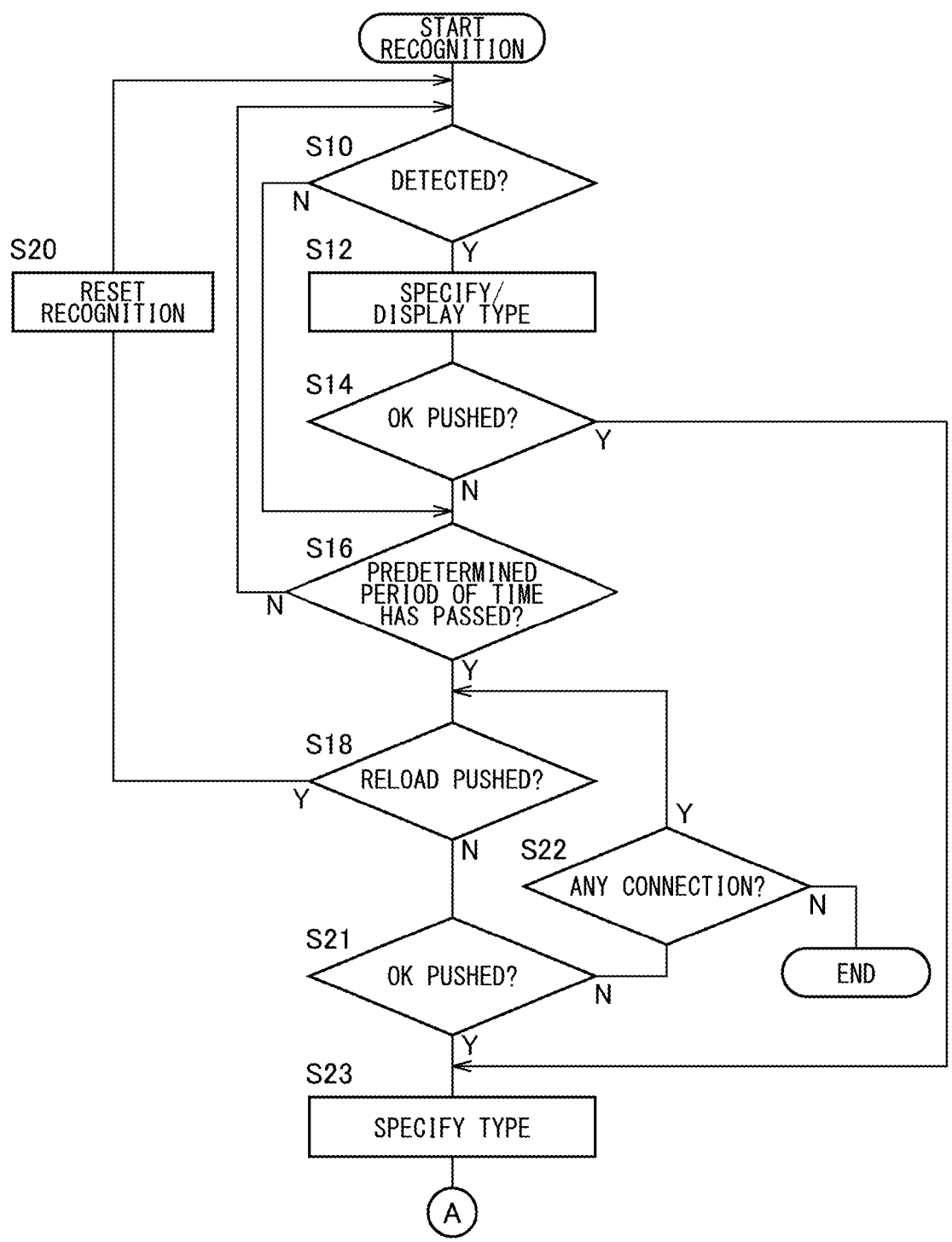
FIG. 15 is a flowchart showing a step for specifying the type of exercise by recognizing an exercise instrument.

The operation step of the exercise instrument controller 12 formed as described above shall be described below. FIG. 15 is a flowchart showing a step for specifying the type of exercise by recognizing an exercise instrument. The recognition of an exercise instrument is started when the communication processing unit 60 is in a connection standby state. When the user holds down a plus button 20a of a muscle electrostimulation device 10 and the communication processing unit 60 detects information received from the muscle electrostimulation device 10 (Y in S10), the type determination unit 61 specifies the type of exercise based on the type of the exercise instrument, and the display control unit 65 displays the type (S12). When an OK button 148 is pushed (Y in S14), the connection of the exercise instrument is confirmed, and the type of the exercise is determined (S22). When the communication processing unit 60 does not detect information from the muscle electrostimulation device 10, S12 and S14 are skipped (N in S10). When the OK button 148 is not pushed (N in S14) and a predetermined period of time has not been passed (N in S16), the step goes back to S10 so as to continue the connection standby state for an exercise instrument. When the predetermined period of time has been passed (Y in S16) and a reload button 149 is pushed (Y in S18), the exercise instrument controller 12 resets all exercise instruments that have been connected at that point, i.e., cancels all the connections (S20), and the step goes back to S10 so as to continue the connection standby state for an exercise instrument. When the reload button 149 is not pushed (N in S18) and the OK button 148 is not pushed, either (N in S21), the exercise instrument controller 12 stands by until either button is pushed when there is an exercise instrument that has already been connected (Y in S22). When there is not even a single exercise instrument that has been connected (N in S22), the exercise instrument controller 12 ends the process of recognizing an exercise instrument. When the OK button 148 is pushed (Y in S21), the connection of the exercise instrument is confirmed, and the type of the exercise is determined (S23). The flow continues to the next figure.

Figure 16:
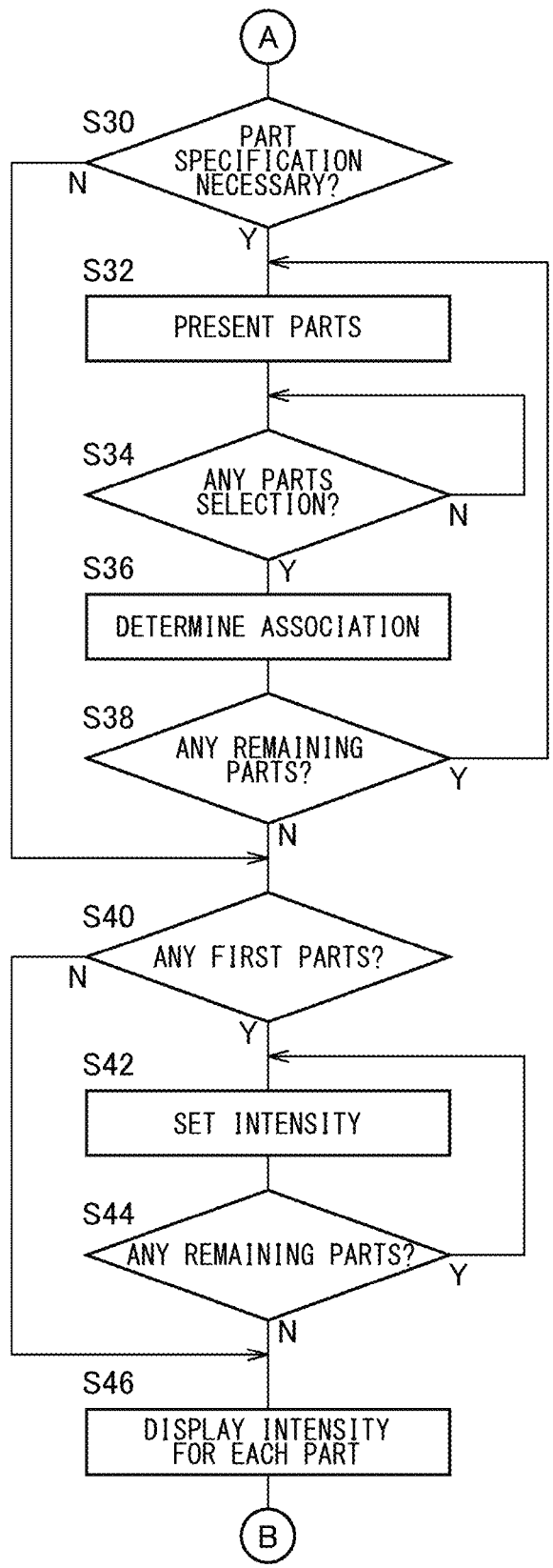
FIG. 16 is a flowchart showing a step for specifying a body part, on which the exercise instrument is used, and the intensity of exercise.

FIG. 16 is a flowchart showing a step for specifying a body part, on which an exercise instrument is used, and the intensity of exercise. When it is necessary to specify a body part for one or a plurality of exercise types that have been specified (Y in S30), the exercise instrument controller 12 presents choices for body parts (S32), stands by until the user selects the body part (N in S34), and, when the user selects the body part (Y in S34), determines the association between the exercise instrument and the body part (S36). When there is other exercise instruments that need the specification of a body part (Y in S38), the step goes back to S32 so as to determine the body part. When there is no other exercise instruments that need the specification of a body part (N in S38), the step proceeds to S40. When no specification of a body part is necessary in S30 (N in S30), the step also skips to S40.

In S40, when there is a body part that does not have any record of setting exercise intensity and that is exercised for the first time (Y in S40), the intensity setting is performed for the body part (S42), and step S42 is repeated when there is another body part for which an intensity setting is to be performed (Y in S44). When there is no body part that is exercised for the first time (N in S40) or when there is no body part left that needs intensity setting (N in S44), the intensity setting for each body part is displayed (S46), and the flow proceeds to the next figure.

Figure 17:
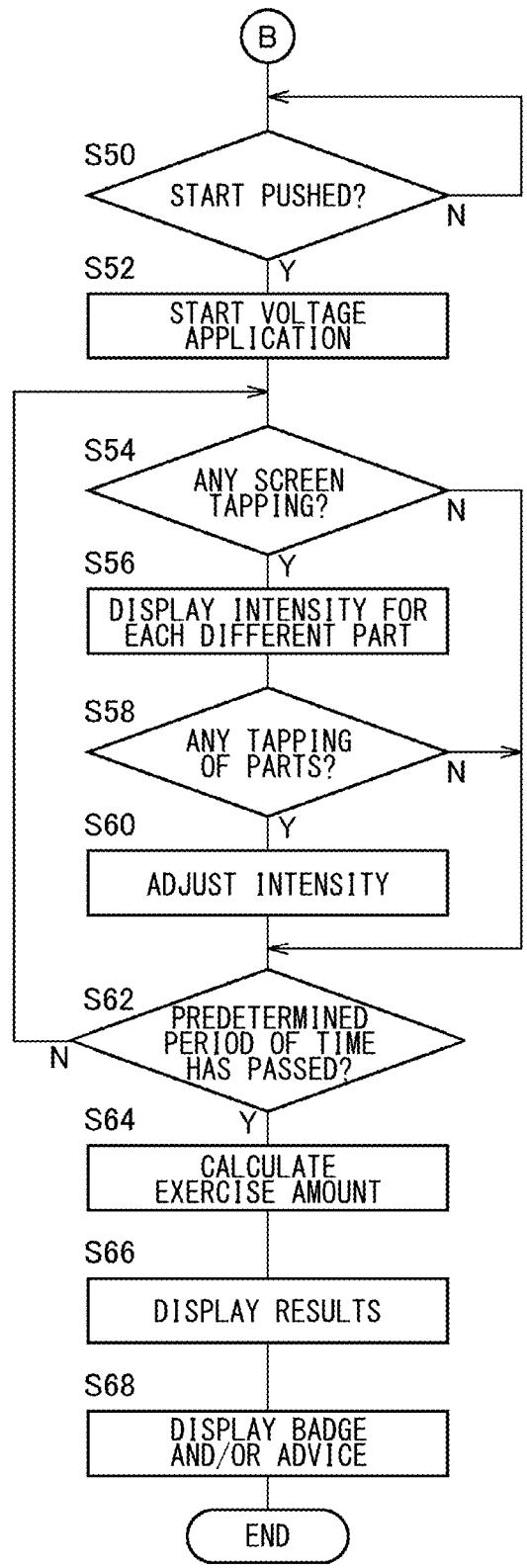
FIG. 17 is a flowchart showing a step during exercise.

FIG. 17 is a flowchart showing a step during exercise. The exercise instrument controller 12 stands by until the user pushes a start button 187 (N in S50), and, when the start button 187 is pushed (Y in S50), the instrument control unit 64 indicates the muscle electrostimulation device 10 to start applying voltage (S52). During the application of voltage, when the pushing (tapping) of a screen by the user is detected (Y in S54), the display control unit 65 displays an intensity confirmation screen 185 for each body part (S56), and when the pushing (tapping) of a body part by the user is detected (Y in S58), the display control unit 65 adjusts the intensity (S60). When there is no pushing of the screen (N in S54) or when there is no pushing of a body part (N in S58), the step is skipped to S62. In S62, when a given predetermined period of time, which is an exercise program time, has not been passed (N in S62), the step goes back to S54, and S54 through S62 are repeated. When the predetermined period of time has been passed (Y in S62), the exercise program is ended, and an exercise amount is calculated (S64). As a result of the exercise, a cumulative exercise amount is displayed (S66). When the cumulative exercise amount exceeds a predetermined value, a badge or advice is displayed so as to finish (S68).

FIG. 18 is a time chart schematically showing the transmission and/or reception of information between the muscle electrostimulation device 10 and the exercise instrument controller 12. In the figure, only transmission and/or reception of information merely as a schematic step, and descriptions of, for example, the repetition of the same operation or the transmission and/or reception of an ACK signal are omitted. When the exercise instrument control program is launched in the exercise instrument controller 12 (S100), the exercise instrument controller 12 turns into a standby state (S102). When the user holds down the plus button 20a of the muscle electrostimulation device 10 (S104) and skin is detected (S106), the muscle electrostimulation device 10 transmits information necessary for communication connection with the exercise instrument controller 12 (S108), and the exercise instrument controller 12 establishes communication with the muscle electrostimulation device 10 (S110). The exercise instrument controller 12 requests the muscle electrostimulation device 10 to transmit information such as the remaining battery capacity (S112), and the muscle electrostimulation device 10 transmits the information such as the remaining battery capacity to the exercise instrument controller 12 (S114).

The exercise instrument controller 12 specifies and then displays, in a list, an exercise instrument or an exercise type (S116) and determines the exercise instrument and the exercise type based on the pushing of the OK button 184 by the user (S118). The exercise instrument controller 12 specifies a body part for each exercise type (S120), sets intensity for each body part (S122), and transmits information regarding the intensity that has been set to the muscle electrostimulation device 10 (S124). The muscle electrostimulation device 10 increases or decreases the set intensity according to an instruction from the exercise instrument controller 12 (S126).

When the start button 187 is pushed in the exercise instrument controller 12 (S128), the exercise instrument controller 12 transmits an instruction to start voltage application to the muscle electrostimulation device 10 (S130), the muscle electrostimulation device 10 starts the voltage application (S132), and the exercise instrument controller 12 displays a screen displayed during exercise (S134). Even during the voltage application, when an instruction to change the intensity setting is given by the user (S136), the exercise instrument controller 12 transmits an instruction to change the intensity to the muscle electrostimulation device 10 (S138), and the muscle electrostimulation device 10 increases or decreases the set intensity according to the instruction (S140). When a predetermined period of time, which is a training time, has passed (S142, S144), the exercise instrument controller 12 transmits an instruction to finish to the muscle electrostimulation device 10 (S148), and the muscle electrostimulation device 10 finishes the voltage application (S150) and transmits a notification indicating the voltage application has been finished to the exercise instrument controller 12 (S152). The exercise instrument controller 12 displays the result of the exercise on a screen so as to finish (S154). As a variation, the exercise instrument controller 12 may not transmit an instruction to finish of S148, and the muscle electrostimulation device 10 may finish the voltage application (S150) when the predetermined period of time has passed (S144) and transmit a notification indicating that the voltage application has been finished to the exercise instrument controller 12. As another variation, the exercise instrument controller 12 may transmit an instruction to finish of S148; however, the muscle electrostimulation device 10 may not transmit a notification indicating that the voltage application has been finished in S152 to the exercise instrument controller 12.

Described above is an explanation of the present invention based on the embodiments. These embodiments are intended to be illustrative only, and it will be obvious to those skilled in the art that various modifications to constituting elements and processes could be developed and that such modifications are also within the scope of the present invention. An exemplary variation is shown in the following.

In the above embodiments, an example has been explained where a muscle electrostimulation device 10, which allows a muscle to be exercised using reflex movements caused by electrostimulation, is used as an exercise instrument. In a variation, the present invention may be applied to a muscle electrostimulation device 10 for hybrid training where reflex movements caused by electrostimulation are superimposed on voluntary movements. In another variation, as an exercise instrument, an instrument other than a muscle electrostimulation device 10 or a device for exercise support may be used. For example, the present invention may be applied for the controlling of a training instrument such as a dumbbell or barbell capable of transmitting and/or receiving exercise count through a wireless communication function. Alternatively, a fastening tool used for Kaatsu (pressurization exercising) training may be provided with a wireless communication function so as to allow for intensity setting.

In the above embodiments, an exercise amount is displayed as the result of exercise. In a variation, a function for registering an image in which a user's face or body type has been captured may be provided, and an image registered before the start of exercise and an image registered after the start of the exercise may be compared with each other and displayed. As another variation, an ultrasonic probe (ultrasonic sensor) may be provided in a muscle electrostimulation device 10, and a cross-sectional image of subcutaneous fat and muscles may be generated based on a detection value thereof and displayed. In addition, a function for sharing the result of exercise through various social media may be provided. These functions allow user's motivation to be kept or increased.

In the above embodiments, for an exercise instrument that can be worn on a plurality of body parts, a body part on which the exercise instrument is used is specified by the user. In a variation, a body part on which the exercise instrument is worn may be determined based on a detection value by a predetermined sensor. For example, a body part may be determined based on a difference in impedance in skin detection or user's record regarding impedance. In another variation, a body part that is the same as that set at the time of the last use may be basically set automatically based on a record, and a new body part is set only when the user instructs to change the part. In another variation, a body part that is in middle of enhancement or a body part that is predicted to lack exercise may be automatically set based on an exercise program and a record. In another variation, an exercise instrument used for a different body part may be specified by the user, and noncontact communication such as NFC may be used for the specification. For example, the specification of an exercise instrument is requested for each body part, and, every time the request is made, the user brings an exercise instrument controller 12 closer to an exercise instrument that is used, and the exercise instrument detected to become closer and the body part are associated with each other. In another variation, an exercise instrument may be specified for each body part by pushing a predetermined button such as the abdominal muscle designation button 20c and the flank designation button 20d of the muscle electrostimulation device 10a. In another variation, the shape of an exercise instrument may be formed in an asymmetrical shape in a vertical or horizontal direction such that the wearing direction is changed depending on a body part on which the exercise instrument is worn. In that case, a body part on which the exercise instrument is worn can be determined by detecting the wearing direction of the exercise instrument. In another variation, a body part on which the exercise instrument is worn may be determined by detecting the length of a fastening belt used when wearing the exercise instrument on a body.

In the above embodiments, explanations have been given of a specification where the exercise instrument controller 12 connects to the information management server 14, transmits information regarding an exercise result for each user and user registration to the information management server 14, and manages the information. In a variation, an exercise instrument control system may be formed of only a plurality of muscle electrostimulation devices 10 and the exercise instrument controller 12 without using the information management server 14.

In the above embodiments, explanations have been given of a specification where exercise time for which voltage is applied or the like is determined as an exercise program. In a variation, an exercise program may be designed such that not only exercise time but also a body part to be used, an exercise frequency or schedule, set intensity, etc., are optimized according to an exercise purpose, a user attribute, an exercise record, etc. In this case, a notification may be issued that requests exercise to be performed according to a proper schedule. Also, automatic adjustment may be performed, for example, where the intensity is gradually increased based on a record or lowered according to the degree of fatigue.

Optional combinations of the aforementioned embodiment and exemplary variations will also be within the scope of the present invention. New embodiments resulting from the combinations will provide the advantages of the embodiment and variations combined.

What is claimed is:

1. An exercise instrument controller comprising:
a communication processing unit that receives information via a predetermined communication means from an exercise instrument used for physical exercise;
a type determination unit that specifies, from among a plurality of types, the type of exercise for which the exercise instrument is used based on the information that has been received;
an association determination unit that specifies association between a body part that is exercised and the exercise instrument based on the type that has been specified;
a setting processing unit that sets an operation detail of the exercise instrument based on manipulation input by the user via a manipulation means;
an instrument control unit that controls, by transmitting information indicating the operation detail via the predetermined communication means for each exercise instrument based on the association between the body part and the exercise instrument that has been specified and the operation detail that has been set, exercise by the exercise instrument; and
a display control unit that controls screen display related to the association between the body part and the exercise instrument, the operation detail, and an exercising status,
wherein, based on a plurality of types of exercise specified for a plurality of exercise instruments, the association determination unit can specify association of the plurality of body parts respectively with different exercise instruments,
wherein the setting processing unit can set different operation details respectively for the plurality of body parts,
wherein the communication processing unit receives information from a plurality of types of exercise instruments, the information that is received having different details for each type of the exercise instruments,
wherein the type determination unit stores, for each type of the exercise instruments, the type of exercise that can be done using an exercise instrument of the type in advance and specifies the type of the exercise by specifying the type of the exercise instrument based on the information that is received, and
wherein the association determination unit stores, for each type of the exercise, one or more body parts that can be exercised according to the type in advance and specifies, in a case where there are a plurality of body parts that can be exercised according to the type of exercise, association between any of the body parts and the exercise instrument based on manipulation input entered via the predetermined manipulation means by the user.

2. The exercise instrument controller according to claim 1,
wherein the exercise instrument is a muscle electrostimulation device that gives electrostimulation to muscles, and
wherein the setting processing unit sets the intensity of the electrostimulation by the muscle electrostimulation device as the operation detail.

3. The exercise instrument controller according to claim 1, wherein the display control unit displays an image of a human body model and displays an image dynamically showing the movement of a muscle being exercised on a screen in accordance with the control status of the exercise instrument.

4. An exercise instrument controller comprising:
a communication processing unit that receives information via a predetermined communication means from an exercise instrument used for physical exercise;
a type determination unit that specifies, from among a plurality of types, the type of exercise for which the exercise instrument is used based on the information that has been received;
an association determination unit that specifies association between a body part that is exercised and the exercise instrument based on the type that has been specified;
a setting processing unit that sets an operation detail of the exercise instrument based on manipulation input by the user via a manipulation means;
an instrument control unit that controls, by transmitting information indicating the operation detail via the predetermined communication means for each exercise instrument based on the association between the body part and the exercise instrument that has been specified and the operation detail that has been set, exercise by the exercise instrument; and
a display control unit that controls screen display related to the association between the body part and the exercise instrument, the operation detail, and an exercising status,
wherein, based on a plurality of types of exercise specified for a plurality of exercise instruments, the association determination unit can specify association of the plurality of body parts respectively with different exercise instruments, and
wherein the setting processing unit can set different operation details respectively for the plurality of body parts,
the exercise instrument controller further comprising an information management unit that determines, as a result of exercise for each body part, the amount of exercise based on an operation detail that has been set and performed for each body part using a coefficient for each body part and records a cumulative exercise amount.

5. An exercise instrument controller comprising:
a communication processing unit that receives information via a predetermined communication means from an exercise instrument used for physical exercise;
a type determination unit that specifies, from among a plurality of types, the type of exercise for which the exercise instrument is used based on the information that has been received;
an association determination unit that specifies association between a body part that is exercised and the exercise instrument based on the type that has been specified;
a setting processing unit that sets an operation detail of the exercise instrument based on manipulation input by the user via a manipulation means;
an instrument control unit that controls, by transmitting information indicating the operation detail via the predetermined communication means for each exercise instrument based on the association between the body part and the exercise instrument that has been specified and the operation detail that has been set, exercise by the exercise instrument; and a display control unit that controls screen display related to the association between the body part and the exercise instrument, the operation detail, and an exercising status, wherein, based on a plurality of types of exercise specified for a plurality of exercise instruments, the association determination unit can specify association of the plurality of body parts respectively with different exercise instruments, wherein the setting processing unit can set different operation details respectively for the plurality of body parts, wherein the association determination unit stores, in advance, a prohibition standard defining a combination of exercise instruments whose use on a single body part or on related body parts is considered to be excessive use and determines whether the use on a body part that can be exercised according to the specified type is considered to be the excessive use defined in the prohibition standard, and wherein the instrument control unit avoids connection to an exercise instrument whose use is considered to be the excessive use.

6. A non-transitory computer readable medium having recorded therein an exercise instrument control program comprising:

a module that receives information via a predetermined communication means from an exercise instrument used for physical exercise;

a module that specifies, by processing by a processor, the type of exercise for which the exercise instrument is used from among a plurality of types based on the information that has been received;

a module that specifies, by processing by the processor, association between a body part that is exercised and the exercise instrument based on the type that has been specified;

a module that sets, by processing by the processor, an operation detail of the exercise instrument based on manipulation input by the user via a predetermined manipulation means;

a module that controls, by transmitting information indicating the operation detail that has been set via the predetermined communication means for each exercise instrument based on the association between the body part and the exercise instrument that has been specified and the operation detail that has been set, exercise by the exercise instrument; and a module that controls screen display related to the association between the body part and the exercise instrument, the operation detail, and an exercising status, wherein in the module that specifies the association, based on a plurality of types of exercise specified for a plurality of exercise instruments, association of the plurality of body parts can be specified respectively with different exercise instruments, wherein in the module that sets the operation detail, different operation details can be set respectively for the plurality of body parts, wherein the module that receives information receives information from a plurality of types of exercise instruments, the information that is received having different details for each type of the exercise instruments, wherein the module that specifies the type of exercise stores, for each type of the exercise instruments, the type of exercise that can be done using an exercise instrument of the type in advance and specifies the type of the exercise by specifying the type of the exercise instrument based on the information that is received, and wherein the module that specifies the association stores, for each type of the exercise, one or more body parts that can be exercised according to the type in advance and specifies, in a case where there are a plurality of body parts that can be exercised according to the type of exercise, association between any of the body parts and the exercise instrument based on manipulation input entered via the predetermined manipulation means by the user.

* * * * *